US010317414B2

(12) United States Patent
Shah et al.

(10) Patent No.: US 10,317,414 B2
(45) Date of Patent: Jun. 11, 2019

(54) PREDICTING CORONARY ARTERY DISEASE AND RISK OF CARDIOVASCULAR EVENTS

(71) Applicant: Duke University, Durham, NC (US)

(72) Inventors: Svati H. Shah, Durham, NC (US); Christopher B. Newgard, Durham, NC (US); William E. Kraus, Durham, NC (US); Elizabeth R. Hauser, Durham, NC (US); Geoffrey S. Ginsburg, Durham, NC (US); L. Kristin Newby, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/066,837

(22) Filed: Mar. 10, 2016

(65) Prior Publication Data

US 2016/0195543 A1    Jul. 7, 2016

Related U.S. Application Data

(63) Continuation of application No. 13/255,568, filed as application No. PCT/US2010/026845 on Mar. 10, 2010, now abandoned.

(Continued)

(51) Int. Cl.
*G16H 50/30* (2018.01)
*G01N 33/68* (2006.01)
(Continued)

(52) U.S. Cl.
CPC .......... *G01N 33/6887* (2013.01); *A61B 5/00* (2013.01); *A61B 5/14532* (2013.01); *A61B 5/14546* (2013.01); *A61B 5/4866* (2013.01); *A61B 5/7275* (2013.01); *G01N 21/78* (2013.01); *G06F 19/00* (2013.01); *G16H 50/30* (2018.01);
(Continued)

(58) Field of Classification Search
None
See application file for complete search history.

(56) References Cited

U.S. PATENT DOCUMENTS

2005/0106104 A1  5/2005  Rosenberg
2007/0077548 A1  4/2007  Boger
(Continued)

FOREIGN PATENT DOCUMENTS

WO    WO 2007/103124    9/2007
WO    2009/014639      1/2009

OTHER PUBLICATIONS

Almasy et al., "Multipoint Quantitative-Trait Linkage Analysis in General Pedigrees," Am J Hum Genet, 1998, vol. 62, pp. 1198-1211.
(Continued)

*Primary Examiner* — Christopher Adam Hixson
*Assistant Examiner* — Michelle Adams
(74) *Attorney, Agent, or Firm* — Michael Best & Friedrich LLP

(57) ABSTRACT

Methods of assessing the risk of cardiovascular disease in a subject by detecting the level of at least one metabolite in a sample from the subject are disclosed herein. The level of the metabolite is indicative of the risk of cardiovascular disease in the subject. The metabolites may be acylcarnitines, amino acids, ketones, free fatty acids or hydroxybutyrate. The cardiovascular disease may be risk of a cardiovascular event, presence of coronary artery disease or risk of development of coronary artery disease.

16 Claims, 6 Drawing Sheets

Related U.S. Application Data

(60) Provisional application No. 61/159,077, filed on Mar. 10, 2009.

(51) Int. Cl.

| | | |
|---|---|---|
| *A61B 5/00* | (2006.01) | |
| *A61B 5/145* | (2006.01) | |
| *G01N 21/78* | (2006.01) | |
| *H01J 49/00* | (2006.01) | |
| *G06F 19/00* | (2018.01) | |
| *G01N 21/77* | (2006.01) | |

(52) U.S. Cl.
CPC .. *H01J 49/0027* (2013.01); *G01N 2021/7786* (2013.01); *G01N 2800/324* (2013.01); *G01N 2800/50* (2013.01); *Y10T 436/174614* (2015.01); *Y10T 436/200833* (2015.01); *Y10T 436/201666* (2015.01)

(56) References Cited

U.S. PATENT DOCUMENTS

| | | |
|---|---|---|
| 2008/0073500 A1 | 3/2008 | Cerda |
| 2011/0318726 A1 | 12/2011 | Shah et al. |

OTHER PUBLICATIONS

An et al., "Hepatic expression of malonyl-CoA decarboxylase reverses muscle, liver and whole-animal insulin resistance," Nat Med, 2004, vol. 10, No. 3, pp. 268-274.
Beekman et al., "Heritabilities of apolipoprotein and lipid levels in three countries," Twin Res, 2002, 5, 87-97.
Brindle et al., "Rapid and noninvasive diagnosis of the presence and severity of coronary heart disease using 1H-NMR-based metabonomics," Nat Med. 2002;8:1439-44.
Chace et al., "Rapid Diagnosis of Maple Syrup Urine Disease in Blood Spots from Newborns by Tandem Mass Spectrometry," Clin Chem, 1995, vol. 41 No. 1, pp. 62-68.
Chace et al.. Use of Tandem Mass Spectrometry for Multiananlyte Screening of Dried Blood Specimens from Newborns. Clinical Chemistry, 2003, vol. 49:11, 1797-1817.
DeLong et al., "Comparing the areas under two or more correlated receiver operating characteristic curves: a nonparametric approach," Biometrics, 1988, vol. 44, No. 3, pp. 837-845.
Ellis et al., Metabolic Fingerprinting as a Diagnostic Tool, Pharmacogenomics, 2007, vol. 8(9).
Ferdinandusse et al., "Identification of the peroxisomal beta-oxidation enzymes involved in the degradation of long-chain dicarboxylic acids," J Lipid Res. 2004;45:1104-11.
Ferrara et al., "Genetic networks of liver metabolism revealed by integration of metabolic and transcriptional profiling," PLoS Genet. 2008;4:e1000034.
Haqq et al., "The Study of the Effects of Diet on Metabolism and Nutrition (STEDMAN) weight loss project: Rationale and design," Contemp Clin Trials, 2005, vol. 26, pp. 616-625.
Hauser et al., "Design of the Genetics of Early Onset Cardiovascular Disease (GENECARD) study," Am Heart J, 2003, 145, pp. 602-613.
Johnson and Wichern D.W., 1988, Applied Multivariate Statistical Analysis. Prentice Hall, Englewood Cliffs, New Jersey.
Kaiser, "The Application of Electronic Computers to Factor Analysis," Educational and Psychological Measurement, 1960, vol. 20, pp. 141-151.
Keurentjes et al., "The genetics of plant metabolism," Nat Genet, 2006;38, pp. 842-849.
Kirschenlohr et al., "Proton NMR analysis of plasma is a weak predictor of coronary artery disease," Nat Med. 2006, 12, pp. 705-710.
Koves et al., "Mitochondrial overload and incomplete fatty acid oxidation contribute to skeletal muscle insulin resistance," Cell Metab, 2008, 7, 45-56.
Koves et al., "Peroxisome proliferator-activated receptor-gamma co-activator 1alpha-mediated metabolic remodeling of skeletal myocytes mimics exercise training and reverses lipid-induced mitochondrial inefficiency," J Biol Chem, 2005, 280, 33588-33598.
Lawlor et al., "(Mis)use of Factor Analysis in the Study of Insulin Resistance Syndrome," Am J Epidemiol, 2004, vol. 159, pp. 1013-1018.
Millington et al., "Tandem mass spectrometry: a new method for acylcarnitine profiling with potential for neonatal screening for inborn errors of metabolism.," J Inherit Metab Dis, 1990, vol. 13, pp. 321-324.
Moselhy et al., "Serum free L-carnitine in association with myoglobin as a diagnostic marker of acute myocardial infarction,"Clinical Biochemistry, Elsevier Inc, US, CA, vol. 42, No. 1-2, Sep. 30, 2008, pp. 78-82, XP025801716.
Muoio et al., "Mechanisms of disease: molecular and metabolic mechanisms of insulin resistance and beta-cell failure in type 2 diabetes," Nat Rev Mol Cell Biol, 2008, 9, 193-205.
Newgard et al., "A branched-chain amino acid-related metabolic signature that differentiates obese and lean humans and contributes to insulin resistance," Cell Metab, 2009, vol. 9, No. 4, pp. 311-326.
Nobukuni et al., "Amino acids mediate mTOR/raptor signaling through activation of class 3 phosphatidylinositol 3OH-kinase," Proc Natl Acad Sci U S A. 2005;102:14238-43.
Patterson et al., "Validation of a new procedure to determine plasma fatty acid concentration and isotopic enrichment," J Lipid Res, 1999, vol. 40, pp. 2118-2124.
Petersen et al., "Mitochondrial dysfunction in the elderly: possible role in insulin resistance," Science, 2003, 300, 1140-1142.
Rissanen, Familial occurrence of coronary heart disease: effect of age at diagnosis. Am J Cardiol, 1979, 44, 60-66.
Rosamond et al., "Heart Disease and Stroke Statistics—2007 Update: A Report From the American Heart Association Statistics Committee and Stroke Statistics Subcommittee," Circulation, 2007;115:e69-171.
Sabatine et al., "Metabolomic identification of novel biomarkers of myocardial ischemia," Circulation. 2005;112:3868-75.
Shah et al., "High heritabilities of serum metabolites and differential metabolomic profiles in families burdened with early onset coronary artery disease," Circulation, vol. 114, No. 18, Suppl. S, Oct. 2006, p. 677, XP002717079.
Shah et al., "High heritability of metabolomic profiles in families burdened with premature cardiovascular disease," Mol Syst Biol, 2009, 5, p. 258.
Shah et al., "Serum lipids in the GENECARD study of coronary artery disease identify quantitative trait loci and phenotypic subsets on chromosomes 3q and 5q," Ann Hum Genet, 2006, 70, 738-748.
Shea et al., "Family history as an independent risk factor for coronary artery disease," J Am Coll Cardiol, 1984, 4, 793-801.
Smith et al., "Determinants of early versus late cardiac death in patients undergoing coronary artery bypass graft surgery," Circulation. 84[5 Suppl], III245-253. 1991.
Um et al., "Nutrient overload, insulin resistance, and ribosomal protein S6 kinase 1, S6K1," Cell Metab. 2006;3:393-402.
World Health Organization The World Health Report 2002—Reducing Risks, Promoting Healthy Life. 2002.
Wu et al., "ENU mutagenesis identifies mice with mitochondrial branched-chain aminotransferase deficiency resembling human maple syrup urine disease," J Clin Invest, 2004, vol. 113, pp. 434-440.
Ferrara, C. T., "Metabolic Pathways of Type 2 Diabetes. Intersection of Genetics, Transcriptomics, and Metabolite Profiling," Dissertation (2008) Department of Pharmacology and Cancer Biology, Duke University (available on ProQuest in 2008).
Nakamura, T. et al., "Can Serum Carnitine Levels Distinguish Hypertrophic Cardiomyopathy From Hypertensive Hearts?" Hypertension, 2000, 36: 215-219.
Search Report from International Patent Application PCT/US2010/026845, dated Apr. 27, 2010.
Chinese Office Action for Application No. 201080021233.X dated Feb. 28, 2014 (9 pages, English translation included).
Chinese Office Action for Application No. 201080021233.X dated May 30, 2013 (Original and Translation, 11 pages).

(56) References Cited

OTHER PUBLICATIONS

Chinese Office Action for Application No. 201080021233.X dated Oct. 30, 2013 (Original and Translation, 11 pages).
Chinese Office Action for Application No. 201080021233.X dated Jul. 28, 2014 (Original and Translation, 7 pages).
European Extended Search Report for Application No. 10751366.5 dated Jan. 2, 2014 (18 pages).
European Patent Office Action for Application No. 10751366.5 dated Jan. 21, 2014 (1 page).
Japanese Office Action for Application No. 2011554159 dated Oct. 29, 2013 (Original and English Translation, 7 pages).
Japanese Office Action for Application No. 2011554159 dated Jun. 10, 2014 (Original and English Translation, 9 pages).
Australian Patent Examination Report No. 1 for Application No. 2010224175 dated Nov. 20, 2014 (3 pages).
United States Patent Office Action for U.S. Appl. No. 13/255,568 dated Jan. 21, 2015 (15 pages).
Japanese Patent Office Action for Application No. 2011-554159 dated Feb. 17, 2015 (4 pages, English translation included).
Chinese Patent Office Action for Application No. 201080021233.X dated Apr. 1, 2015 (10 pages, English translation included).
Australian Patent Examination Report No. 2 for Application No. 2010224175 dated Aug. 12, 2015 (3 pages).
United States Patent Office Final Action for U.S. Appl. No. 13/255,568 dated Sep. 10, 2015 (17 pages).
Canadian Patent Office Action for Application No. 2,755,050 dated Oct. 14, 2017 (4 pages).
Australian Patent Examination Report No. 1 for Application No. 2015258285 dated Sep. 21, 2016 (2 pages).
Shah et al., "Baseline metabolomic profiles predict cardiovascular events in patients at risk for coronary artery disease." American Heart Journal, 163, May 5, 2012, 844-850.
International Search Report and Written Opinion for Application No. PCT/US2016/022388 dated May 26, 2016 (13 pages).
Neubauer S. "The Failing Heart—An Engine Out of Fuel," N Engl J Med. 2007, 1140-1151.
Sharma Kand Kass DA. "Heart Failure With Preserved Ejection Fraction Mechanisms, Clinical Features, and Therapies," Circulation Research. 2014, 79-96.
Shah SH, Kraus WE, Newgard CB. "Metabolomic Profiling for the Identification of Novel Biomarkers and Mechanisms Related to Common Cardiovascular Diseases Form and Function," Circulation. 2012, 1110-1120.
Shah SH et al. "Association of a Peripheral Blood Metabolic Profile WithCoronary Artery Disease and Risk of Subsequent Cardiovascular Events," Circ Cardiovasc Genet. 2010, 207-214.
Aguer C et al. "Acylcarnitines: potential implications for skeletal muscle insulin resistance," FASEB, Journal. 2015, 336-345.
Lum H et al. "Plasma Acylcarnitines Are Associated With Physical Performance in Elderly Men," J Gerontal A Biol Sci Med Sci. May 2011; 66A (5):548-553.
Shah A et al. "Metabolic profiles predict adverse events after coronary artery bypass grafting," JTCS. 2012, 872-878.
Australian Patent Examination Report No. 2 for Application No. 2015258285 dated Jul. 14, 2017 (4 pages).
Canadian Patent Office Action for Application No. 2,755,050 dated Jun. 14, 2017 (4 pages).
Indian Patent Office Examination Report for Application No. 3737/KOLNP/2011 dated May 31, 2018 (6 pages).
United States Patent Office Action for U.S. Appl. No. 15/557,621 dated Jun. 27, 2018 (9 pages).
Heather et al., "A Practical guide to metabolomic profiling as a discovery tool for human heart disease," Journal of Molecular and Cellular Cardiology, 2013, 55:2-11.
United States Patent Office Action for Application No. 15/557,621 dated Feb. 6, 2019 (9 pages).

PREDICTING CORONARY ARTERY DISEASE AND RISK OF CARDIOVASCULAR EVENTS

CROSS-REFERENCE TO RELATED APPLICATIONS

This patent application is a continuation of U.S. patent application Ser. No. 13/255,568, filed on Sep. 9, 2011, which is a national stage filing under 35 U.S.C. 371 of International Patent Application No. PCT/US2010/26845, filed Mar. 10, 2010, which claims the benefit of U.S. Provisional Patent Application No. 61/159,077, filed Mar. 10, 2009, the contents of each of which is incorporated herein by reference in its entirety.

BACKGROUND OF THE INVENTION

Coronary artery disease (CAD) is the leading cause of death in industrialized countries, and in concert with the epidemic of obesity and diabetes, is rapidly becoming the leading cause of death in developing countries. The genetic predilection of CAD is well-established; family history has been shown to be an independent risk factor for CAD, especially in early onset forms. Despite this, the genetic architecture of CAD remains largely unknown.

Many accepted risk factors for CAD are metabolic. However, there remains an incomplete mechanistic understanding of CAD risk, and equally important, a need to refine our ability to identify individuals at highest risk of cardiovascular events. Given the complex nature of CAD, evaluation with more comprehensive tools may improve risk stratification and enhance our understanding of the disease process.

SUMMARY OF THE INVENTION

In one aspect, methods for assessing risk of cardiovascular disease in a subject are provided. The risk assessment may include predicting the likelihood a subsequent cardiovascular event such as a myocardial infarction, predicting development of CAD, or discriminating the presence of CAD in a subject. The methods include detecting at least one metabolite in a sample from the subject. The metabolite may be an acylcarnitine, an amino acid, a ketone, a free fatty acid or β-hydroxybutyrate. The levels of metabolites are then compared to a standard or to control subjects and can be used to determine the level of risk of a cardiovascular event, the risk of development of CAD or the presence of CAD in the subject.

In another aspect, methods of developing a treatment plan for a subject with or at risk of developing CAD or a subject at risk for a cardiovascular event arc also provided. The methods include using the level of detected metabolite in the subject to develop a treatment plan based on the risk of cardiovascular disease in the subject. The plan may include diet, exercise and pharmaceutical treatment options.

In still another aspect, methods for assessing the risk of cardiovascular disease in a subject are provided in which a sample is obtained from the subject. The sample is provided to a laboratory for detection of metabolite levels in the sample. The metabolites detected may be acylcarnitines, amino acids, ketones, fatty acids or hydroxybutyrate. The laboratory returns a report indicating metabolite levels in the sample, which are indicative of the risk of cardiovascular disease in the subject.

DETAILED DESCRIPTION

Figure 1:
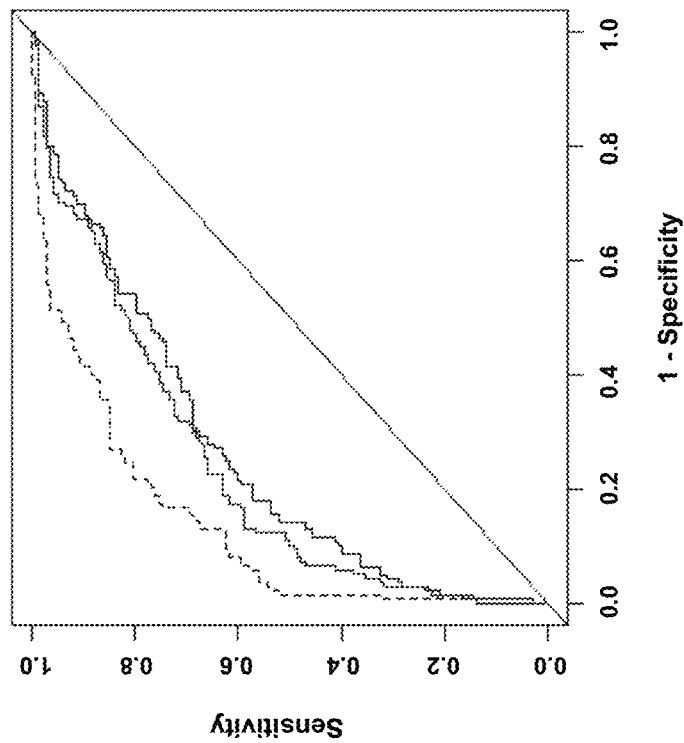
FIG. 1 is a set of graphs showing the receiver operating characteristic (ROC) curves for metabolite factors and CAD. ROC curves and measures of model fit (c-statistic) are presented for three models: a clinical model inclusive of traditional CAD risk factors (diabetes, hypertension, dyslipidemia, smoking, BMI, family history; and for the replication group, age, race and sex are also included) (black line); a model inclusive of all traditional risk factors plus metabolite factors 4 and 9 (gray line); and a model inclusive of all traditional risk factors plus all metabolite factors (dashed black line). The top graph shows the initial group and the bottom graph shows the replication group.
Figure 1:
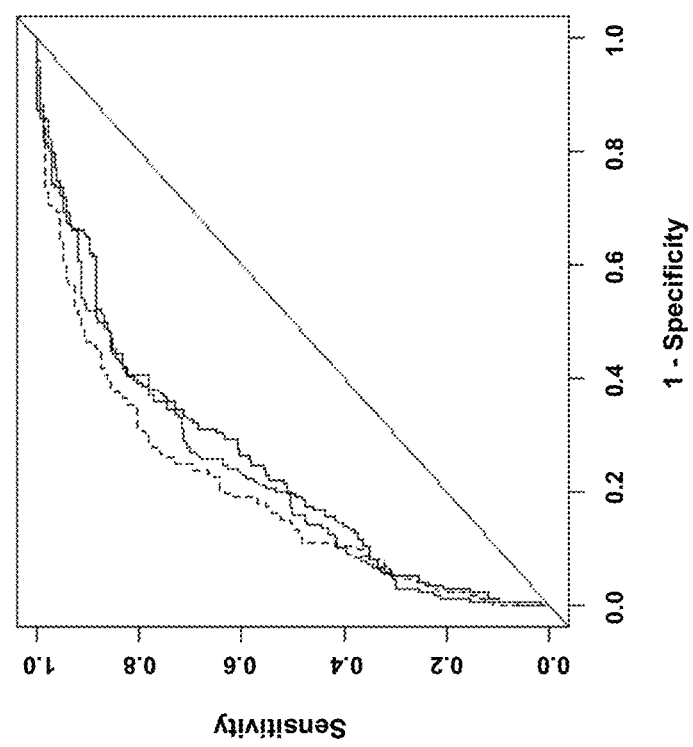

Metabolomics, the study of small-molecule metabolites, may be useful for diagnosis of human disease. Studies have demonstrated heritability of metabolites in plants and mice. As described in the Examples, metabolite profiles are heritable in human families with early-onset CAD, suggesting that the known heritability of CAD may be mediated at least in part through metabolic components measurable in blood. The Examples describe quantitative profiling of 69 metabolites, including acylcarnitine species (byproducts of mitochondrial fatty acid, carbohydrate and amino acid oxidation), amino acids and conventional metabolites such as free fatty acids, ketones and β-hydroxybutyrate, in participants enrolled in the Duke CATHGEN biorepository and in families selected from the Duke GENECARD study. The capability of metabolite profiles to assess the risk of cardiovascular disease in a subject is provided herein. The Examples demonstrate that the levels of particular metabolites, alone or in combination, discriminate the likelihood of developing CAD, the presence of CAD and the risk of subsequent cardiovascular events.

Methods of assessing or predicting risk of cardiovascular disease in a subject are provided. The methods include detecting the level of at least one metabolite in a sample from the subject. The amount or relative level of the metabolite may be detected. The metabolites detected may be acylcarnitines, amino acids, ketones, free fatty acids (FFA), or hydroxybutyrate. The level of the metabolite in the sample from the subject is then compared to a standard to assess the risk of cardiovascular disease. The standard may be an empirically derived number for each metabolite indicating a normal range and/or a range indicative of cardiovascular disease or may be direct comparison to the levels of metabolite in individuals with known cardiovascular disease status.

Methods for assessing the risk of cardiovascular disease in a subject by obtaining a sample from the subject and providing the sample to a laboratory for detection of metabolite levels in the sample are also provided. As above, the metabolite detected by the laboratory may include acylcarnitines, amino acids, ketones, fatty acids and hydroxybutyrate. A report indicating metabolite levels in the sample is then received from the laboratory. The report indicates the level of the metabolite in the subject and the level can be used to compare to standard values to indicate the risk of cardiovascular disease in the subject.

The risk of cardiovascular disease includes assessing the risk of a subject without CAD developing CAD over time due to heritable factors, assessing the presence or absence of CAD in a subject and assessing the risk of having a cardiovascular event. Cardiovascular events include myocardial infarction, stroke and death.

Subjects may be any mammal, suitably the subject is human. Subjects identified as having or at risk of developing CAD may be further assessed to determine their risk of a cardiovascular event using the methods provided herein. The methods may be used to help diagnose the presence of CAD in a non-invasive fashion and/or to develop a treatment plan for subjects identified as at risk for CAD, having CAD or at risk for a cardiovascular event. The treatment plan may include provision of dietary, exercise, and pharmaceutical therapies to the subject. A cardiovascular event includes, but is not limited to, myocardial infarction (MI), stroke and death.

The metabolite may be detected using a variety of samples, several of which will be apparent to those skilled in the art. In the Examples, peripheral blood was obtained from the subject and processed in order to detect the level of metabolites in the subject. Other tissues or fluids from the subject may also be used, including but not limited to blood, plasma, urine, serum, saliva, and tissue biopsies.

Any method may be used to detect the metabolite. Suitably the method is quantitative such that the level or amount of the metabolite in the subject or a sample from the subject may be determined. In the Examples, the level of the metabolites was detected by mass spectrometry. Other methods of measurement may be used, including nuclear magnetic resonance (NMR). The metabolites may also be detected using colorimetric or fluorometric assays based on detection of the metabolite by an assay such as a binding or enzymatic assay. Any suitable assay method for the metabolites may be used. Such methods will be apparent to those skilled in the art. The level of the metabolite in the subject may be reported as ng/ml of metabolite in blood or tissue, by the mM or μM concentration of the metabolite in the blood or tissue or by using arbitrary units to show relative levels amongst subjects. In the Examples, the mM or μM of metabolite in the blood are reported.

In some embodiments, detection of a single metabolite is sufficient to assess risk of cardiovascular disease. In other embodiments, 2, 3, 4, 5, 7, 10, 15, 20, 25, 30, 35, 40, 45, 50, 55, 60 or 65 metabolites may be detected and used in the methods to assess the risk of cardiovascular disease. The metabolites detected may be related in a factor by principal component analysis of a population of subjects. The factors, or groups of metabolites, useful for assessing heritability of CAD and for the presence of CAD or risk of having a cardiovascular event are presented in the Examples below.

The level of metabolite in the subject is used to determine whether the subject has CAD, risk of the subject developing CAD and/or the risk of the subject experiencing a cardiovascular event in the future. The level of risk determination may be based on a standard level of the metabolite present in the blood. Such a standard is used for the relationship between HDL and LDL cholesterol measurements in which risk for CAD is predicted when cholesterol levels reach certain level in the blood after fasting and the ratio of HDL to LDL is beyond standard limits. Such standards are generally developed based on a large population study. Alternatively, the determination of risk may be based on direct comparison to one or more control subjects. For example, a set of control subjects lacking CAD and with no cardiovascular events in the two years following sample procurement and a set of control subjects with CAD and with or without a cardiovascular event in the two years following sample procurement could be used as a comparison.

The risk of cardiovascular disease in the subject may be expressed in relative terms. For instance a normal level of a metabolite may be referred to as 1.0 in subjects at low to average risk for cardiovascular disease such as CAD or a cardiovascular event. Any numbers below 1.0 could indicate the subject has a lower risk than the general population risk. A number greater than 1.0 would indicate that the subject has a greater than average risk level and the actual number could relate to the level of risk. For example, a subject whose metabolite level is 2.0 may be two times as likely to experience a cardiovascular event in the next two years as compared to an average individual.

The assessment of risk of cardiovascular disease, including CAD or a future cardiovascular event, includes but is not limited to, developing a risk profile. The assessment or prediction may indicate that the subject is 10%, 20%, 30%, 40%, 50%, 60%, 70%, 80%, 90%, 100%, 200%, 300%, 400%, 500%, 750% or 1000% more likely to have or develop a cardiovascular disease, such as CAD or have cardiovascular event, than a control subject. A control subject is an individual that does not have CAD and possesses levels of the metabolite that do not correlate with an increased risk of CAD or a cardiovascular event.

The metabolites predictive of risk of developing cardiovascular disease CAD include metabolites involved in many of the major pathways of lipid, protein and carbohydrate metabolism. Thus, the acylcarnitines include acetyl carnitine (C2), a by-product of glucose, fatty acid and amino acid metabolism, Propionyl carnitine (C3) and Isoveleryl carnitine (C5), which provide information on amino acid catabolism, the dicarboxylated acylcarnitine, which report on peroxisomal fatty acid metabolism, and the medium-long chain acylcarnitines, which are intermediates in long-chain fatty acid beta-oxidation. The amino acids serve as important intermediates in protein turnover and catabolism and the ketones are an index of fatty acid beta-oxidation. Table 1 below shows the short and full-names of the metabolites tested in the Examples. Table 2 shows the biological functions, if available, of each of the tested metabolites.

TABLE 1

Nomenclature and Intra-Individual Variability of Metabolites. Metabolite short names, full names, and measures of intra-individual variability are presented.

| Short Name | Full Metabolite Name | Measures of Intra-Individual Variability | |
|---|---|---|---|
| | | $R^2$ | CV |
| C2 | Acetyl carnitine | 0.84 | 5.16 |
| C3 | Propionyl carnitine | 0.75 | 22.95 |
| C4:Ci4 | Butyryl carnitine or Isobutyryl carnitine | 0.75 | 13.48 |
| C5:1 | Tiglyl carnitine | 0.46 | 11.24 |
| C5 | Isovaleryl carnitine, 3-methylbutyryl carnitine or 2-Methylbutyryl carnitine | 0.51 | 13.08 |
| C4-OH | β-Hydroxy-butyryl carnitine | 0.40 | 15.46 |
| Ci4-DC:C4DC | Methylmalonyl carnitine or Succinyl carnitine | NA | NA |
| C8:1 | Octenoyl carnitine | 0.86 | 11.29 |
| C8 | Octanoyl carnitine | 0.96 | 4.49 |
| c8:1-OH/C6:1-DC | 3-Hydroxy-cis-5-octenoyl carnitine or Hexenedioyl carnitine | NA | NA |
| C8:1-DC | Octenedioyl carnitine | NA | NA |
| C5-DC | Glutaryl carnitine | 0.60 | 10.33 |
| C6-DC | Adipoyl carnitine | 0.54 | 13.33 |
| C10:3 | Decatrienoyl carnitine | 0.74 | 8.78 |
| C10:1 | Decenoyl carnitine | 0.99 | 3.57 |
| C10 | Decanoyl carnitine | 0.90 | 8.3 |
| C10OH:C8DC | 3-Hydroxy-decanoyl carnitine or Suberoyl carnitine | 0.91 | 6.47 |
| C12:1 | Dodecenoyl carnitine | 0.91 | 8.07 |
| C12 | Lauroyl carnitine | 0.48 | 12.54 |
| C12OH:C10DC | 3-Hydroxy-dodecanoyl carnitine or Sebacoyl carnitine | 0.94 | 3.16 |
| C14:2 | Tetradecadienoyl carnitine | 0.89 | 4.25 |
| C14:1 | Tetradecenoyl carnitine | 0.74 | 4.62 |
| C14:1-OH | 3-Hydroxy-tetradecenoyl carnitine | 0.74 | 4.8 |
| C14-OH:12-DC | 3-Hydroxy-tetradecanoyl carnitine or Dodecanedioyl carnitine | 0.68 | 4.91 |
| C16 | Palmitoyl carnitine | 0.36 | 7.83 |
| C16-OH:C14-DC | 3-Hydroxy-hexadecanoyl carnitine or Tetradecanedioyl carnitine | 0.95 | 3.98 |
| C16:2 | Hexadecadienoyl carnitine | NA | NA |
| C16:1 | Palmitoleoyl carnitine | NA | NA |
| C16:1-OH/C14:1-DC | 3-Hydroxy-palmitoleoyl carnitine or cis-5-Tetradecenedioyl carnitine | NA | NA |
| C18:2 | Linoleyl carnitine | 0.84 | 4.33 |
| C18:1 | Oleyl carnitine | 0.90 | 4.77 |
| C18 | Stearoyl carnitine | 0.53 | 6.08 |
| C18:2-OH | 3-Hydroxy-linoleyl carnitine | NA | NA |
| C18:1-OH | 3-Hydroxy-octadecenoyl carnitine | NA | NA |
| C18-OH:C16-DC | 3-Hydroxy-octadecanoyl carnitine or Hexadecanedioyl carnitine, thapsoyl carnitine | 0.70 | 7.91 |
| C20 | Arachidoyl carnitine, eicosanoyl carnitine | 0.65 | 4.49 |
| C20:1-OH/C18:1-DC | Octadecenedioyl carnitine | 0.66 | 8.46 |
| C20-OH/C18-DC | 3-Hydroxy-eicosanoyl carnitine or Octadecanedioyl carnitine | 0.39 | 9.42 |
| C20:4 | Arachidonoyl carnitine | NA | NA |
| C22 | Behenoyl carnitine, docosanoyl carnitine | 0.84 | 5.16 |
| GLY | Glycine | 0.85 | 1.36 |
| ALA | Alanine | 0.97 | 0.49 |
| SER | Serine | 0.79 | 2.14 |
| PRO | Proline | 0.68 | 1.11 |
| VAL | Valine | 0.84 | 1.25 |
| LEU/ILE | Leucine/Isoleucine | 0.95 | 0.79 |
| MET | Methionine | 0.95 | 1.45 |
| HIS | Histidine | 0.33 | 2.04 |
| PHE | Phenylalanine | 0.95 | 0.72 |
| TYR | Tyrosine | 0.94 | 1.61 |
| ASX | Aspartic acid/asparagine | 0.88 | 1.55 |
| GLX | Glutamine/glutamate | 0.55 | 2.33 |
| ORN | Ornithine | 0.86 | 1.54 |
| CIT | Citrulline | 0.57 | 4.69 |
| ARG | Arginine | 0.98 | 1.37 |
| FFA | Total free fatty acids | 0.99 | 14.1 |
| HBUT | β-hydroxybutyrate | 0.90 | 4.8 |
| KET | Ketones | 0.91 | 3.7 |

TABLE 2

Biological functions of the metabolites measured. By measuring conventional metabolites such as fatty acids, ketones and beta-hydroxybutyrate, a large panel of acylcarnitines and fifteen of the biologically relevant amino acids, the panel of metabolites surveyed report on the major pathways of lipid, protein and carbohydrate metabolism. This table displays biological functions (when available) of each of the individual metabolites measured.

| Metabolite | β-oxidation of fatty acids | ω-oxidataion of fatty acids | Ketogenesis | Cholesterol & chol transport | Canonical 20 amino acids of polypeptides | Urea cycle | Branched chain amino acid catabolism | Glycolysis & Krebs Cycle | Other function(s)/ related conditions |
|---|---|---|---|---|---|---|---|---|---|
| C2 | x | | | | | | | | |
| C3 | x? | | | | | | x | | Propionyl-CoA carboxylase deficiency |
| C4:CI4 | x | | | | | | x | | |
| C5:1 | | | | | | | x | | |
| C5 | x? | | | | | | x | | |
| C4-OH | x | | x | | | | | | |
| C14-DC:C4DC | | x | | | | | x | x | |
| C8:1 | x | | | | | | | | |
| C8 | x | | | | | | | | |
| C8:1-OH/C6:1-DC | x | x | | | | | | | |
| C8:1-DC | x | x | | | | | | | |
| C5-DC | | x? | | | | | | | Glutaric acidermia type1 unable to break down completely the amino acids lysine, hydroxylysine and tryptophan. |
| C6-DC | | x | | | | | | | 3-methylglutaryl carnitine_HMGCo4 lyase deficiency |
| C10:3 | x | | | | | | | | |
| C10:1 | x | | | | | | | | |
| C10 | x | | | | | | | | |
| C10OH:C8DC | x | x | | | | | | | |
| C12:1 | x | | | | | | | | |
| C12 | x | | | | | | | | |
| C12OH:C10DC | x | x | | | | | | | |
| C14:2 | x | | | | | | | | |
| C14:1 | x | | | | | | | | |
| C14:1-OH | | | | | | | | | |
| C14-OH:12-DC | x | x | | | | | | | |
| C16 | x | | | | | | | | |
| C16-OH:C14-DC | x | x | | | | | | | |
| C16:2 | x | | | | | | | | |
| C16:1 | x | | | | | | | | |
| C16:1-OH/C14:1-DC | x | x | | | | | | | |
| C16:2 | x | | | | | | | | |
| C16:1 | x | | | | | | | | |
| C16 | x | | | | | | | | |
| C16:2-OH | x | | | | | | | | |
| C18:1-OH | x | | | | | | | | |
| C18-OH:C16-DC | x | x | | | | | | | |
| C20 | x | | | | | | | | |
| C20:1-OH/C18:1-DC | x | x | | | | | | | |
| C20-OH/C18-DC | x | x | | | | | | | |
| C20:4 | x | x | | | | | | | Eicosanoids |
| C22 | x | | | | | | | | |
| GLY | | | | | x | | | | Neurotransmitter, glutathione |
| ALA | | | | | x | | | | Transaminations |
| SER | | | | | x | | | | Purines, pyrimidines |
| PRO | | | | | x | | | | |
| VAL | | | | | x | | x | | |
| LEU/ILE | | | | | x | | x | | |
| MET | | | | | x | | | | Carnitine, taurine, 1-carbon metabolism, phospholipids, homocysteine |
| HIS | | | | | x | | | | Histamine |
| PHE | | | | | x | | | | Neurotransmitters |
| TYR | | | | | x | | | | Neurotransmitters melanin |
| ASX | | | | | x | x | | | Neurotransmitters, nitrogen transport |

TABLE 2-continued

Biological functions of the metabolites measured. By measuring conventional metabolites such as fatty acids, ketones and beta-hydroxybutyrate, a large panel of acylcarnitines and fifteen of the biologically relevant amino acids, the panel of metabolites surveyed report on the major pathways of lipid, protein and carbohydrate metabolism. This table displays biological functions (when available) of each of the individual metabolites measured.

| Metabolite | β-oxidation of fatty acids | ω-oxidation of fatty acids | Ketogenesis | Cholesterol & chol transport | Canonical 20 amino acids of polypeptides | Urea cycle | Branched chain amino acid catabolism | Glycolysis & Krebs Cycle | Other function(s)/related conditions |
|---|---|---|---|---|---|---|---|---|---|
| GLX | | | | | x | x | | | Transaminations, nitrogen transport, glutathione, neurotransmitters |
| ORN | | | | | | x | | | Polyamines |
| CIT | | | | | | x | | | |
| ARG | | | | | x | x | | | Nitric oxide |
| FFA | x | x | | | | | | | |
| HBUT | | | x | | | | | | |
| KET | | | x | | | | | | |

Methods of predicting the risk of a cardiovascular event (death or myocardial infarction) in a subject by detecting at least one metabolite in the subject are also provided. The metabolites predictive of risk of a cardiovascular event are presumed products of peroxisomal fatty acid metabolism, in particular the short-chain dicarboxyl acylcarnitines, and citrulline. The specific metabolites are listed in Table 9 of the Examples and are identified as factor 8. Table 10 shows the individual metabolites within Factor 8 and provides the Factor load data for each metabolite. The data in the Examples demonstrate that citrulline and the short-chain dicarboxyl acylcarnitines are predictive of the risk of a cardiovascular event.

Individual metabolites may also be predictive of the risk of a cardiovascular event. These metabolites include Gly, Ala, Ser, Pro, Met, His, Phe, Tyr, Asx, Glx, Ornithine, Citrulline, arg, C2, C3, C4:C14; C5:1, C5, C4:OH, C14-DC:C4DC, C5-DC, C6-DC, C10:3, C10, C10-OH:C8DC, C12:1, C12, C12-OH:C10DC, C14:1-OH, C14-OH:C12-DC, C16, C16-OH/C14-DC, C18:2, C18-OH/C16-DC, C20, C20:1-OH/C18:1-DC, C20-OH/C18-DC, C8:1-OH/C6:1-DC, C8:1-DC, C16:1, C16:1-OH/C14:1-DC, C20:4, FFA, HBUT, and Ket. In particular, the levels of citrulline, C5-DC, C6-DC, C8:1-OH/C6:1-DC, and C8:1-DC are predictive of cardiovascular events. In addition, the levels of ornithine, citrulline, C5, C14-DC:C4DC, C5-DC, C6-DC, C10-OH:C8DC, C8:1-OH/C6:1-DC, C8:1-DC, C20:4 and FFA are also useful for assessing the risk of a cardiovascular event.

Methods of assessing the presence and/or extent of CAD in a subject by detecting the level of at least one metabolite in a sample from the subject are also provided. The metabolites useful for assessing the presence of CAD are medium-chain acylcarnitine, a branched chain amino acid or associated metabolite, or a metabolite associated with the urea cycle.

The specific metabolites are listed in Table 6, 7 and 8 of the Examples and are identified as factors 1, 4, and 9 in Table 9. Table 10 shows the individual metabolites within Factors 1, 4 and 9 and provides the Factor load data for each metabolite. Only those metabolites with factor loads greater than or equal to 0.04 are included in the factor.

Individual metabolites may also be predictive of the risk of a cardiovascular event. These metabolites include Pro, Leu/Ile, Met, Val, Glx, Citrulline, C2, C3, C4:Ci4; C5, C8, C8:1-OH/C6:1-DC, C10:1, C14:2, C14:1-OH, C16:2, C16:1, C16:2, C16:1, C16:1-OH/C14:1-DC, C18-OH/C16-DC, HBUT, and Ket. In particular, the levels of Leu/Ile, Glx, C2, C14:1-OH and C16:1-OH/C14:1-DC are indicative of the presence of CAD in a subject. Increased levels of Leu/Ile or Glx as compared to normal controls or a normal standard are indicative of CAD in the subject. Decreases levels of C2, C14:1-OH and C16:1-OH/C14:1-DC are indicative of the presence of CAD in a subject. A level of Leu/Ile greater than 165 mM, 170 mM or 175 mM is indicative of coronary artery disease. A level of Glx greater than 127 mM, 128 mM, 129 mM, 130 mM, 132 mM, 135 mM or 140 mM is indicative of coronary artery disease. A level of C14:1-OH less than 0.01404, 0.013 µM or 0.012 µM is indicative of coronary artery disease. A level of C16:1-OH/C14:1-DC less than 0.009 µM, 0.0089 µM, or 0.0088 µM is indicative of coronary artery disease.

Methods of assessing the likelihood of developing CAD in a subject by detecting the level of at least one metabolite in a sample from the subject are also provided. The metabolites useful for assessing the likely development of CAD are the short- and medium-chain acylcarnitine metabolites, branched chain amino acids and urea cycle related metabolites.

The specific metabolites are listed in Table 14 of the Examples. Table 15 shows the individual metabolites within the identified Factors. Only those metabolites with factor loads greater than or equal to 0.04 are included in the factor. Individual metabolites may also be predictive of the risk of a cardiovascular event. These metabolites include ketones, arg, ornithine, citrulline, glx, ala, val, leu/ile, pro, C2, C14:1, C18:1, C5:1, C4-i4, C18, C10:1 and FFA.

The Examples below are meant to be illustrative and not to limit the scope of the invention.

EXAMPLES

Example 1: Association of Metabolites with CAD and Risk of Cardiovascular Events Methods Study Sample The CATHGEN biorepository consists of subjects recruited sequentially through the cardiac catheterization laboratories at Duke University Medical Center (Durham, N.C.). After informed consent, blood was obtained from the femoral artery at time of arterial access for catheterization, immediately processed to separate plasma, and frozen at −80° C. All subjects were fasting for a minimum of six hours prior to collection. Clinical data were provided by the DDCD, a database of patients undergoing cardiac catheterization at Duke University since 1969. Medication data were collected for medications used chronically, i.e. medications at admission (inpatients) or from a clinic note within one month prior (outpatients). Follow-up data, including occurrence of myocardial infarction (MI) and death were collected at six months after catheterization, then annually thereafter. Vital status was confirmed through the National Death Index. The indication for catheterization for all subjects was clinical concern for ischemic heart disease. Patients with severe pulmonary hypertension or organ transplant were excluded.

To evaluate the discriminative capability of metabolites for CAD, two independent case-control groups were constructed: 'initial' (174 CAD cases and 174 CAD-free controls); and 'replication' (140 CAD cases and 140 CAD-free controls). For the initial group, sequential cases meeting inclusion criteria were selected: CADindex ≥32 (at least one coronary artery with ≥95% stenosis) and age-of-onset ≤55 years. CADindex is a numerical summary of angiographic data. (Smith et al., Circulation 1991; 84[5 Suppl], 111:245-253.) Age-of-onset was defined as age at first MI, percutaneous coronary intervention (PCI), coronary artery bypass grafting (CABG), or age at first catheterization meeting CADindex threshold. Sex- and race-matched controls meeting the following criteria were selected: CADindex ≤23; no coronary artery with >50% stenosis; age-at-catheterization ≥61 years; and no history of MI, PCI, CABG, or transplant. Given the differences in age based on these criteria, results could be confounded by age. Therefore, for the replication group, sequential cases and controls meeting the same inclusion criteria were selected, but the criterion of age-of-onset (cases) or age-at-catheterization (controls) was removed and cases/controls were not matched. This allowed generalizability of findings to a representative population of patients referred for catheterization. Analyses were also performed by constraining CAD cases to those with a previous history of MI (N=86 cases in initial, N=61 cases in replication).

To evaluate the capability of metabolites to predict risk of subsequent cardiovascular events, an 'event' group was constructed, combining CAD cases from the initial and replication groups ('event' group, N=314); of these, 74 individuals suffered death or MI during follow-up. To validate findings for the association of metabolites with risk of cardiovascular events, profiling was performed in an independent cardiovascular event case-control group ('event-replication') composed of unique individuals from CATHGEN meeting the following criteria: ejection fraction >40%; no history of PCI or CABG; and no subsequent CABG. Among these, event cases (N=63) suffered death or MI, or had PCI with acute coronary syndrome within two years after catheterization; controls (N=66) were event-free, with at least two years of follow-up, and were matched to cases on age, race, sex and CADindex.

The Duke Institutional Review Board approved the protocols for CATHGEN and the current study. Informed consent was obtained from each subject.

Metabolite Measurements

Fasting plasma samples were used for quantitative determination of targeted levels for 45 acylcarnitines, 15 amino acids, five conventional analytes (total, low-density[LDL] and high-density lipoprotein [HDL] cholesterol, triglycerides and glucose), ketones, β-hydroxybutyrate, total free fatty acids and C-reactive protein [CRP] (Table 1). Methodology and coefficients of variation for each assay have been reported. (Shah et al., Mol Syst Biol 2009; 5:258 and Newgard et al., Cell Metab 2009; 9(4):311-26.) The laboratory (Sarah W. Stedman Nutrition and Metabolism metabolomics/biomarker core laboratory) was blinded to case-control status and cases/controls were randomly distributed.

Standard clinical chemistry methods were used for conventional metabolites with reagents from Roche Diagnostics (Indianapolis, Ind.), and for free fatty acids (total) and ketones (total and β-hydroxybutyrate) with reagents from Wako. All assays were performed on a Hitachi 911 clinical chemistry analyzer.

For mass spectroscopy (MS)-profiled metabolites (acylcarnitines, amino acids) the following protocol was used. (An et al., Nat Med 2004; 10(3):268-74 and Chace et al., Clin Chem 1995; 41(1):62-8.) Proteins were first removed by precipitation with methanol. Aliquoted supernatants were dried, and then esterified with hot, acidic methanol (acylcarnitines) or n-butanol (amino acids). Analysis was done using tandem MS with a Quattro Micro instrument (Waters Corporation, Milford, Mass.). Quantification of the "targeted" intermediary metabolites was facilitated by addition of mixtures of known quantities of stable-isotope internal standards (Table 3). Leucine/isoleucine (LEU/ILE) are reported as a single analyte because they are not resolved by our MS/MS method, and include contributions from allo-isoleucine and hydroxyproline. Under normal circumstances these isobaric amino acids contribute little to the signal attributed to LEU/ILE. In addition, the acidic conditions used to form butyl esters results in partial hydrolysis of glutamine to glutamic acid and of asparagine to aspartate. Accordingly, values that are reported as GLU/GLN (CLX) or ASP/ASN (ASX) are not meant to signify the molar sum of glutamate and glutamine, or of aspartate and asparagine, but rather measure the amount of glutamate or aspartate plus the contribution of the partial hydrolysis reactions of glutamine and asparagine, respectively. Biological annotation is included in Table 2 above.

TABLE 3

Internal spiked standards for acylcarnitine and amino acid measurements.

| Amino Acids | Acylcarnitines | Free Fatty Acids |
| --- | --- | --- |
| $^{15}N_1, ^{13}C_1$-glycine | $D_3$-acetyl carnitine | $D_3$-octanoate |
| $D_4$-alanine | $D_3$-propionyl carnitine | $D_3$-decanoate |
| $D_8$-valine | $D_3$-butyryl carnitine | $D_3$-laurate |
| $D_7$-proline | $D_9$-isovaleryl carnitine | $D_3$-myristate |
| $D_3$-serine | $D_3$-octanoyl carnitine | $D_3$-palmitate |
| $D_3$-leucine | $D_3$-palmitoyl carnitine | $^{13}C_1$-oleate |
| $D_3$-methionine | | $D_3$-stearate |
| $D_5$-phenylalanine | | |
| $D_4$-tyrosine | | |
| $D_3$-aspartate | | |
| $D_3$-glutamate | | |
| $D_2$-ornithine | | |
| $D_2$-citrulline | | |
| $D_5$-arginine | | |

Statistical Analysis

Metabolite levels reported as "0" (i.e., below the lower limits of quantification (LOQ)) were given a value of LOQ/2. Metabolites with >25% of values as "0" were not analyzed (five acylcarnitines). All metabolites were natural log-transformed to approximate a normal distribution. For analysis of CAD status, generalized linear regression models were used to assess differences in metabolite levels between CAD cases and controls, both unadjusted and adjusted for traditional CAD risk factors not constrained by matching: diabetes, hypertension, dyslipidemia, body-mass-index (BMI), family history of CAD, and smoking. Analyses of the replication group were further adjusted for race, sex and age. With log transformation, all significant metabolites showed a normal distribution (Kolmogorov-Smirnov test P>0.01), except valine, ketones, and C8, C8:1-OH/C6:1-DC, C10:1, C14:2, C16:1, C16:1-OH/C14:1-DC, and C18-OH/C16-DC acylcarnitines. Visual inspection of the distributions suggested a grossly normal distribution. Regardless, we performed sensitivity analyses using non-parametric Wilcoxon tests, showing similar results as the semi-parametric linear models, except for valine and C14:2 acylcarnitine, both of which were not significant in linear regressions (p=0.10 and p=0.06, respectively), but were significant with these non-parametric tests (p=0.05 and p=0.008). Analyses were also stratified by diabetes and smoking.

In exploratory analyses, multivariable models were further adjusted for medication classes (beta-blockers, statins, diabetes medications, aspirin, angiotensin-converting-enzyme inhibitors, nitrates, clopidogrel and diuretics), use of pre-procedural sedation, and continuous intravenous heparin use at time of catheterization. The CATHGEN protocol requires sample collection prior to supplemental heparin administration during catheterization. Therefore, adjustment for continuous intravenous heparin use at time of catheterization addresses differences related to heparin. Only 66% of individuals had medication data, hence medications were coded as a discrete variable: not on medication, missing, and on medication.

Given that metabolites reside in overlapping pathways, correlation of metabolites is expected. We used principal components analysis (PCA) to reduce the large number of correlated variables into uncorrelated factors. Factors with higher "eigenvalues" account for larger amounts of variability within the dataset. Factors with an eigenvalue >1.0 were identified and varimax rotation performed to produce interpretable factors. Metabolites with a factor load ≥|0.4| were reported as composing a factor. See Table 10. Scoring coefficients were constructed from the initial group and used to calculate factor scores for each individual (weighted sum of the standardized metabolites within that factor, weighted on the factor loading for each metabolite), and were also applied to the replication group. Generalized linear regression models were used to assess the difference in factor scores between cases and controls. All factors were normally distributed (Kolmogorov-Smirnov test P>0.01), except for factors 7-9; visual inspection showed a grossly normal distribution. Non-parametric Wilcoxon tests for these factors showed the same results as linear models.

To further assess the independent capability of metabolite profiles to discriminate CAD cases from controls, multivariable logistic regression models were constructed; in these models, CAD risk factors (BMI, dyslipidemia, hypertension, diabetes, family history, smoking) were forced into the model, then metabolite factors were added. Receiver operating curves (ROC) were constructed and measures of model fit calculated. Nonparametric analysis for comparison of the areas under these curves was performed using previous methods. (DeLong et al., Biometrics 1988; 44(3):837-45.)

For analysis of subsequent cardiovascular events, cases from initial and replication groups were pooled ('event' group). The relationship between metabolite factors and time-to-occurrence of death/MI was assessed using Cox proportional hazards (unadjusted and adjusted for BMI, dyslipidemia, hypertension, diabetes, family history, smoking, age, race, sex, creatinine, ejection fraction and CADindex). The assumption of proportional hazards was met. For replication in the 'event-replication' group, scoring coefficients from PCA-derived factors constructed in the initial CAD group were used to calculate factor scores in the event-replication group; logistic regression was used to assess the association between factors and case/control status (unadjusted and adjusted for BMI, dyslipidemia, hypertension, diabetes, family history, smoking, creatinine, and ejection fraction).

As all analyses were exploratory in nature and given co-linearity of the metabolites, two-sided p-values unadjusted for multiple comparisons are presented; however, results interpreted in the context of Bonferroni correction are reported. Nominal statistical significance was defined as P≤0.05. Bonferroni corrected p-values were P<0.0007 (individual metabolites) and P<0.004 (factors). Statistical analyses were performed by D.R.C. and S.H.S. using SAS version 9.1 (Cary N.C.).

Results

Patient Populations

Population characteristics for the initial (174 early-onset CAD cases, 174 matched controls) and replication groups (140 CAD cases, 140 controls) are displayed in Table 4, and for the event-replication group in Table 5.

TABLE 4

Baseline Clinical Characteristics of Initial and Replication Groups.

|  | Initial Group | | Replication Group | |
| --- | --- | --- | --- | --- |
|  | Cases (N = 174) | Controls (N = 174) | Cases (N = 140) | Controls (N = 140) |
| Age (mean [SD]) | 48.7 (10.0) | 67.8 (5.9) | 61.1 (13.0) | 60.3 (13.0) |
| Age-of-onset | 45.8 (6.9) | N/A | 57.0 (10.8) | N/A |
| Sex (% male) | 77.0% | 75.3% | 75.0% | 51.4% |
| Race (% white) | 66.9% | 67.8% | 77.5% | 76.9% |
| Hypertension | 64.9% | 68.4% | 72.9% | 64.3% |
| Diabetes | 32.2% | 23.0% | 28.6% | 19.3% |
| Family history of CAD | 57.5% | 22.4% | 49.3% | 32.9% |
| Currently smoking (%) | 66.1% | 47.1% | 64.3% | 39.3% |
| Body mass index (mean [SD]) | 31.1 (6.8) | 29.3 (6.0) | 29.1 (5.8) | 31.4 (9.1) |
| CADindex (mean [SD]) | 56.5 (21.9) | 6.2 (9.4) | 58.6 (21.8) | 4.6 (8.6) |

TABLE 4-continued

Baseline Clinical Characteristics of Initial and Replication Groups.

|  | Initial Group | | Replication Group | |
| --- | --- | --- | --- | --- |
|  | Cases (N = 174) | Controls (N = 174) | Cases (N = 140) | Controls (N = 140) |
| No. of coronary arteries w/≥75% stenosis | | | | |
| 0 | 0% | 100% | 0% | 100% |
| 1 | 27.0% | 0% | 22.1% | 0% |
| 2 | 29.3% | 0% | 35.0% | 0% |
| 3 | 43.7% | 0% | 42.9% | 0% |
| Ejection fraction (mean [SD]) | 51.8 (13.0) | 59.4 (13.0) | 53.5 (15.1) | 63.4 (9.5) |
| History of MI | 49.4% | 0% | 42.9% | 0% |
| History of dyslipidemia | 73.6% | 44.8% | 60.7% | 49.3% |
| Total cholesterol (mean [SD]) | 178.5 (55.1) | 176.1 (39.2) | 177.9 (44.4) | 169.9 (38.7) |
| LDL cholesterol (mean [SD]) | 105.3 (39.3) | 104.2 (32.1) | 105.9 (36.8) | 101.1 (32.5) |
| HDL cholesterol (mean [SD]) | 35.6 (10.8) | 48.0 (16.0) | 39.3 (12.2) | 39.0 (12.6) |
| Triglycerides (mean [SD]) | 157.7 (170.4) | 93.2 (60.7) | 128.1 (82.4) | 119.8 (91.1) |

TABLE 5

Baseline Clinical Characteristics of the Event Replication Group.

|  | Overall (N = 129) | Event Cases (N = 63) | No Event Controls (N = 66) | P-value* |
| --- | --- | --- | --- | --- |
| Age (mean [SD]) | 62.9 (10.4) | 63.2 (10.7) | 62.7 (10.1) | 0.81 |
| Sex (% male) | 54.3% | 54.0% | 54.6% | 0.95 |
| Race (% white) | 74.2% | 72.1% | 76.2% | 0.57 |
| Hypertension | 72.1% | 77.8% | 66.7% | 0.16 |
| Diabetes | 31.8% | 33.3% | 30.3% | 0.71 |
| Family history of CAD | 32.6% | 27.0% | 37.9% | 0.19 |
| Currently smoking (%) | 51.2% | 44.4% | 53.0% | 0.33 |
| Body mass index (mean [SD]) | 30.0 (7.6) | 30.5 (8.5) | 29.4 (6.6) | 0.42 |
| CADindex (mean [SD]) | 28.6 (12.4) | 28.9 (12.0) | 28.3 (12.8) | 0.81 |
| No. of coronary arteries w/≥75% stenosis |  |  |  | 0.96 |
| 0 | 15.1% | 15.0% | 15.2% |  |
| 1 | 63.5% | 63.3% | 63.6% |  |
| 2 | 19.1% | 20.0% | 18.2% |  |
| 3 | 2.4% | 1.7% | 3.0% |  |
| Ejection fraction (mean [SD]) |  | 61.0 (9.2) | 61.8 (8.8) | 0.63 |
| History of MI |  | 0% | 0% | NA |
| History of dyslipidemia |  | 55.6% | 54.6% | 0.91 |
| Total cholesterol (mean [SD]) |  | 166.6 (44.2) | 168.7 (49.0) | 0.81 |
| LDL cholesterol (mean [SD]) |  | 104.5 (34.2) | 108.0 (28.6) | 0.70 |
| HDL cholesterol (mean [SD]) |  | 49.0 (16.4) | 51.6 (22.2) | 0.59 |
| Triglycerides (mean [SD]) |  | 117.0 (94.9) | 108.5 (113.9) | 0.36 |

*p-value for difference between subjects with events and event-free controls.

Association of Individual Metabolites with CAD

Levels of several amino acids were different between cases and controls in the initial group (Table 6), including the branched-chain amino acids leucine/isoleucine (P<0.0001) and valine (P=0.007), glutamate/glutamine (P<0.0001), proline (P=0.04) and methionine (P=0.05). Levels of several acylcarnitines were also different between cases and controls in the initial group, including the C16 acylcarnitines (C16:1, P=0.006; C16:1-OH/C14:1-DC, P=0.004; C16:2, P=0.05; and C18-OH/C16-DC, P=0.003), and C4:Ci4 (P=0.009), C8 (P=0.009), C8:1-OH/C6:1-DC (P=0.003), and C10:1 (P=0.002) acylcarnitine (Table 6). For most metabolites, these differences persisted after adjustment for CAD risk factors.

TABLE 6

Association of Individual Metabolites with CAD. Means and standard deviations for metabolites significantly different between cases and controls in the initial group are presented. Results for these analytes in the replication group are also presented. All values are in millimolar for amino acids and micromolar for acylcarnitines. Analytes in bold show consistent association across both datasets (with consistent direction of effect).

| Metabolite | Initial Group | | | | Replication Group | | | |
| --- | --- | --- | --- | --- | --- | --- | --- | --- |
| | CAD Cases | Controls | Unadj p | Adj p* | Cases | Controls | Unadj p | Adj p† |
| Amino Acids | | | | | | | | |
| PRO | 190.2 (56.4) | 177.5 (41.3) | 0.04 | 0.13 | 197.0 (75.9) | 173.9 (44.3) | 0.001 | 0.03 |
| LEU/ILE | 175.1 (39.5) | 158.7 (36.3) | <0.0001 | 0.004 | 183.6 (52.7) | 162.3 (35.5) | <0.0001 | 0.002 |
| VAL | 259.1 (58.1) | 242.2 (54.9) | 0.007 | 0.26 | 256.8 (63.7) | 266.2 (51.5) | 0.10 | 0.05 |
| MET | 25.8 (5.6) | 24.6 (4.8) | 0.05 | 0.14 | 26.6 (7.7) | 24.0 (5.2) | 0.003 | 0.03 |
| GLX | 151.1 (41.7) | 125.5 (39.0) | <0.0001 | <0.0001 | 129.7 (30.5) | 120.3 (31.4) | 0.005 | 0.02 |
| CIT | 36.4 (12.2) | 39.9 (11.2) | 0.002 | 0.003 | 39.7 (12.0) | 37.8 (10.8) | 0.21 | 0.86 |
| Acylcarnitines | | | | | | | | |
| C2 | 9.10 (4.25) | 9.90 (3.98) | 0.02 | 0.01 | 10.73 (4.86) | 8.76 (3.83) | <0.0001 | <0.0001 |
| C4:Ci4 | 0.22 (0.12) | 0.18 (0.10) | 0.009 | 0.03 | 0.22 (0.11) | 0.20 (0.11) | 0.06 | 0.15 |
| C5 | 0.104 (0.095) | 0.087 (0.047) | 0.01 | 0.08 | 0.092 (0.045) | 0.101 (0.045) | 0.05 | 0.004 |
| C8 | 0.107 (0.057) | 0.123 (0.076) | 0.009 | 0.04 | 0.129 (0.121) | 0.124 (0.106) | 0.54 | 0.17 |
| C8:1-OH/C6:1-DC | 0.030 (0.027) | 0.032 (0.019) | 0.003 | 0.005 | 0.026 (0.013) | 0.028 (0.012) | 0.47 | 0.56 |
| C10:1 | 0.174 (0.097) | 0.193 (0.083) | 0.002 | 0.002 | 0.200 (0.096) | 0.198 (0.096) | 0.87 | 0.47 |
| C14:2 | 0.039 (0.027) | 0.044 (0.028) | 0.02 | 0.02 | 0.039 (0.028) | 0.047 (0.025) | 0.06 | 0.42 |
| C14:1-OH | 0.012 (0.006) | 0.014 (0.007) | 0.04 | 0.03 | 0.012 (0.006) | 0.015 (0.007) | 0.002 | 0.006 |
| C16:2 | 0.0088 (0.0065) | 0.0092 (0.0053) | 0.05 | 0.03 | 0.0098 (0.0059) | 0.0117 (0.007) | 0.03 | 0.11 |
| C16:1 | 0.0258 (0.0171) | 0.0262 (0.0124) | 0.006 | 0.07 | 0.0286 (0.0154) | 0.0321 (0.0138) | 0.03 | 0.24 |
| C16:1-OH/C14:1-DC | 0.0087 (0.0036) | 0.0091 (0.0031) | 0.004 | 0.01 | 0.0088 (0.0040) | 0.0096 (0.0040) | 0.008 | 0.01 |
| C18-OH/C16-DC | 0.008 (0.009) | 0.007 (0.004) | 0.003 | 0.02 | 0.007 (0.003) | 0.008 (0.004) | 0.005 | 0.03 |
| Ketones | 289.8 (345.0) | 324.3 (286.0) | 0.04 | 0.14 | 319.2 (289.9) | 313.1 (279.0) | 0.87 | 0.44 |
| β-hydroxybutyrate | 199.7 (271.6) | 237.1 (235.3) | 0.01 | 0.05 | 211.5 (205.7) | 202.9 (199.8) | 0.63 | 0.29 |

*adjusted for diabetes, hypertension, smoking, dyslipidemia, family history of CAD, BMI.
†adjusted for age, race, sex, diabetes, hypertension, smoking, dyslipidemia, family history of CAD, BMI Several of these metabolites were also significant in the replication group in adjusted analyses (with similar direction of effect), including the amino acids leucine/isoleucine and glutamate/glutamine, and the long-chain acylcarnitines C14:1-OH and C16:1-OH/C14:1-DC (Table 6). In unadjusted analyses, these metabolites, amino acids methionine and proline, and C16:2 and C16:1 acylcarnitine were significant in both groups.

Further adjustment for lipids (total, LDL, and HDL cholesterol and triglycerides) resulted in similar results, although with attenuation of association for LEU/ILE in the initial group (Tables 7 and 8). Analyses stratified by diabetes suggested some heterogeneity of association by diabetes. For example, LEU/ILE and C16:1-OH/C14:1-DC showed stronger association in non-diabetics. Analyses stratified by smoking suggested no difference in smokers and non-smokers.

TABLE 7

Association of Individual Metabolites with CAD in the Initial Group. Means
and standard deviations for all individual metabolites for the overall initial group, as well as
stratified by CAD, are presented. All values are in millimolar for amino acids and micromolar
for acylcarnitines. P-values are for the association between metabolites and CAD in
unadjusted and adjusted analyses. Analytes in bold show consistent association across both
datasets in adjusted analyses (with consistent direction of effect).

|  | Overall | | CAD Cases | | CAD Controls | | | | |
|---|---|---|---|---|---|---|---|---|---|
|  | Mean | SD | Mean | SD | Mean | SD | Unadjusted | Adjusted* | Adjusted p† |
| Amino Acids | | | | | | | | | |
| GLY | 311.48 | 77.87 | 308.33 | 76.16 | 316.85 | 79.53 | 0.23 | 0.57 | 0.20 |
| ALA | 324.98 | 87.49 | 333.56 | 94.24 | 316.19 | 79.76 | 0.12 | 0.51 | 0.37 |
| SER | 93.59 | 20.53 | 100.16 | 20.30 | 97.21 | 20.64 | 0.15 | 0.09 | 0.39 |
| PRO | 183.78 | 49.65 | 190.17 | 56.43 | 177.56 | 41.28 | 0.04 | 0.13 | 0.56 |
| VAL | 250.59 | 57.02 | 259.08 | 58.13 | 242.16 | 54.94 | 0.007 | 0.26 | 0.84 |
| LEU/ILE | 166.94 | 38.70 | 175.12 | 39.47 | 158.74 | 36.32 | <0.0001 | 0.004 | 0.30 |
| MET | 25.17 | 5.26 | 25.75 | 5.58 | 24.56 | 4.83 | 0.05 | 0.14 | 0.92 |
| HIS | 60.95 | 13.09 | 60.57 | 13.76 | 61.10 | 12.43 | 0.71 | 0.63 | 0.30 |
| PHE | 65.36 | 12.93 | 66.57 | 13.28 | 64.12 | 12.52 | 0.09 | 0.29 | 0.60 |
| TYR | 61.65 | 15.05 | 62.56 | 15.72 | 60.95 | 14.18 | 0.37 | 0.47 | 0.16 |
| ASX | 108.58 | 23.06 | 110.70 | 23.54 | 108.89 | 22.30 | 0.12 | 0.54 | 0.94 |
| GLX | 138.17 | 42.23 | 151.07 | 41.68 | 125.46 | 39.02 | <0.0001 | <0.0001 | 0.02 |
| ORN | 75.14 | 23.31 | 77.53 | 24.08 | 72.75 | 22.41 | 0.08 | 0.15 | 0.92 |
| CIT | 38.23 | 11.85 | 38.44 | 12.17 | 39.86 | 11.21 | 0.002 | 0.003 | 0.003 |
| ARG | 70.54 | 20.74 | 71.25 | 22.16 | 69.58 | 19.01 | 0.84 | 0.29 | 0.86 |
| Acylcarnitines | | | | | | | | | |
| C2 | 9.499 | 4.123 | 9.105 | 4.249 | 9.900 | 3.976 | 0.02 | 0.01 | 0.01 |
| C3 | 0.469 | 0.243 | 0.496 | 0.270 | 0.438 | 0.210 | 0.06 | 0.63 | 0.72 |
| C4:C14 | 0.200 | 0.113 | 0.216 | 0.116 | 0.183 | 0.104 | 0.009 | 0.03 | 0.81 |
| C5.1 | 0.057 | 0.034 | 0.057 | 0.035 | 0.056 | 0.031 | 0.90 | 0.62 | 0.97 |
| C5 | 0.096 | 0.075 | 0.104 | 0.094 | 0.067 | 0.047 | 0.01 | 0.08 | 0.88 |
| C4:OH | 0.056 | 0.039 | 0.058 | 0.045 | 0.054 | 0.032 | 0.89 | 0.62 | 0.70 |
| C14-DC:C4DC | 0.052 | 0.033 | 0.055 | 0.039 | 0.049 | 0.024 | 0.53 | 0.48 | 0.43 |
| C8:1 | 0.262 | 0.145 | 0.271 | 0.164 | 0.253 | 0.123 | 0.69 | 0.50 | 0.12 |
| C8 | 0.115 | 0.068 | 0.107 | 0.067 | 0.123 | 0.076 | 0.009 | 0.04 | 0.04 |
| C5-DC | 0.044 | 0.045 | 0.045 | 0.062 | 0.043 | 0.019 | 0.29 | 0.53 | 0.15 |
| C6-DC | 0.085 | 0.131 | 0.084 | 0.181 | 0.075 | 0.042 | 0.86 | 0.73 | 0.07 |
| C10:3 | 0.125 | 0.076 | 0.125 | 0.063 | 0.125 | 0.067 | 0.37 | 0.24 | 0.11 |
| C10:1 | 0.154 | 0.090 | 0.174 | 0.095 | 0.193 | 0.083 | 0.002 | 0.002 | 0.0002 |
| C10 | 0.223 | 0.164 | 0.200 | 0.154 | 0.245 | 0.207 | 0.05 | 0.14 | 0.00 |
| C10-OH:C8DC | 0.035 | 0.026 | 0.034 | 0.028 | 0.035 | 0.023 | 0.11 | 0.37 | 0.11 |
| C12:1 | 0.120 | 0.069 | 0.117 | 0.075 | 0.122 | 0.062 | 0.12 | 0.48 | 0.05 |
| C12 | 0.075 | 0.053 | 0.074 | 0.059 | 0.075 | 0.047 | 0.32 | 0.84 | 0.11 |
| C12-OH:C10DC | 0.009 | 0.007 | 0.008 | 0.007 | 0.009 | 0.007 | 0.10 | 0.23 | 0.07 |
| C14:2 | 0.043 | 0.026 | 0.041 | 0.025 | 0.046 | 0.027 | 0.02 | 0.02 | 0.01 |
| C14:1 | 0.051 | 0.050 | 0.078 | 0.049 | 0.085 | 0.051 | 0.53 | 0.07 | 0.05 |
| C14:1-OH | 0.014 | 0.007 | 0.013 | 0.006 | 0.015 | 0.007 | 0.04 | 0.03 | 0.009 |
| C14-OH/C12-DC | 0.010 | 0.005 | 0.010 | 0.006 | 0.010 | 0.005 | 0.78 | 0.20 | 0.10 |
| C16 | 0.086 | 0.025 | 0.087 | 0.026 | 0.085 | 0.024 | 0.59 | 0.43 | 0.98 |
| C16-OH/C14-DC | 0.007 | 0.005 | 0.006 | 0.005 | 0.007 | 0.005 | 0.40 | 0.25 | 0.07 |
| C18:2 | 0.074 | 0.038 | 0.072 | 0.038 | 0.075 | 0.039 | 0.40 | 0.24 | 0.21 |
| C18:1 | 0.154 | 0.063 | 0.150 | 0.058 | 0.157 | 0.069 | 0.30 | 0.32 | 0.24 |
| C18 | 0.044 | 0.015 | 0.043 | 0.014 | 0.046 | 0.015 | 0.22 | 0.34 | 0.25 |
| C18:1-OH/C16:1-DC | 0.010 | 0.006 | 0.010 | 0.006 | 0.010 | 0.007 | 0.46 | 0.04 | 0.03 |
| C18-OH/C16-DC | 0.009 | 0.008 | 0.010 | 0.009 | 0.008 | 0.005 | 0.003 | 0.02 | 0.09 |
| C20 | 0.009 | 0.007 | 0.008 | 0.007 | 0.009 | 0.009 | 0.22 | 0.20 | 0.13 |
| C20:1-OH/C18:1-DC | 0.010 | 0.009 | 0.011 | 0.011 | 0.009 | 0.009 | 0.65 | 0.54 | 0.89 |
| C20-OH/C18-DC | 0.010 | 0.010 | 0.011 | 0.014 | 0.009 | 0.005 | 0.26 | 0.76 | 0.92 |
| C22 | 0.009 | 0.008 | 0.009 | 0.008 | 0.006 | 0.007 | 0.24 | 0.69 | 0.00 |
| C8:1-OH/C6:1-DC | 0.031 | 0.021 | 0.029 | 0.025 | 0.032 | 0.017 | 0.003 | 0.005 | <.0001 |
| C8:1-DC | 0.029 | 0.022 | 0.029 | 0.027 | 0.026 | 0.014 | 0.24 | 0.97 | 0.23 |
| C16:2 | 0.012 | 0.007 | 0.012 | 0.007 | 0.013 | 0.009 | 0.05 | 0.03 | 0.09 |
| C16:1 | 0.029 | 0.015 | 0.027 | 0.016 | 0.030 | 0.015 | 0.006 | 0.07 | 0.05 |
| C16:1-OH/C14:1-DC | 0.010 | 0.054 | 0.009 | 0.005 | 0.010 | 0.004 | 0.004 | 0.01 | 0.003 |
| C18:2-OH | 0.014 | 0.009 | 0.014 | 0.008 | 0.014 | 0.006 | 0.82 | 0.42 | 0.81 |
| C20:4 | 0.011 | 0.007 | 0.011 | 0.007 | 0.011 | 0.006 | 0.91 | 0.92 | 0.78 |
| Other | | | | | | | | | |
| Total free fatty acids | 1.13 | 0.59 | 1.09 | 0.61 | 1.18 | 0.56 | 0.11 | 0.08 | 0.28 |
| Ketones | 306.49 | 315.4 | 289.82 | 345.01 | 324.29 | 285.96 | 0.04 | 0.14 | 0.73 |
| β-hydroxybutyrate | 218.01 | 254.14 | 199.72 | 271.84 | 237.06 | 235.30 | 0.01 | 0.05 | 0.54 |

*adjusted for diabetes, hypertension, smoking, dyslipidemia, family history of CAD, BMI.
†adjusted for diabetes, hypertension, smoking, dyslipidemia, family history of CAD, BMI, and total, LDL, HDL cholesterol and triglycerides.

TABLE 8

Association of Individual Metabolites with CAD in the Replication Group.
Means and standard deviations for all individual metabolites for the overall replication group,
as well as stratified by CAD, are presented. All values are in millimolar for amino acids and
micromolar for acylcarnitines. P-values are for the association between metabolites and CAD
in unadjusted and adjusted analyses. Analytes in bold show consistent association across both
datasets in adjusted analyses (with consistent direction of effect).

| | Overall | | CAD Cases | | CAD controls | | P-values | | |
|---|---|---|---|---|---|---|---|---|---|
| | Mean | SD | Mean | SD | Mean | SD | Unadjusted | Adjusted* | Adjusted p† |
| Amino Acids | | | | | | | | | |
| GLY | 315.81 | 88.31 | 320.30 | 73.59 | 311.33 | 82.54 | 0.34 | 0.58 | 0.57 |
| ALA | 322.45 | 101.97 | 338.60 | 112.14 | 314.31 | 90.34 | 0.25 | 0.29 | 0.70 |
| SER | 103.65 | 26.15 | 104.12 | 29.34 | 103.18 | 22.81 | 0.99 | 0.52 | 0.34 |
| PRO | 185.45 | 63.10 | 197.04 | 75.89 | 173.67 | 44.28 | 0.001 | 0.03 | 0.04 |
| VAL | 281.47 | 58.00 | 258.77 | 53.88 | 266.17 | 51.49 | 0.10 | 0.05 | 0.04 |
| LEU/ILE | 172.94 | 46.10 | 163.63 | 52.68 | 152.26 | 35.50 | <.0001 | 0.002 | 0.002 |
| MET | 25.31 | 8.88 | 26.58 | 7.73 | 24.03 | 5.16 | 0.003 | 0.53 | 0.04 |
| HIS | 65.53 | 13.86 | 66.25 | 14.26 | 67.41 | 13.47 | 0.42 | 0.55 | 0.14 |
| PHE | 66.18 | 13.46 | 69.20 | 14.70 | 63.16 | 11.40 | 0.0003 | 0.002 | 0.0006 |
| TYR | 64.58 | 15.17 | 65.72 | 17.11 | 63.41 | 12.90 | 0.39 | 0.45 | 0.34 |
| ASX | 98.44 | 26.06 | 114.16 | 23.81 | 82.64 | 17.67 | <.0001 | <.0001 | <.0001 |
| GLX | 125.01 | 31.25 | 129.72 | 30.46 | 128.38 | 31.43 | 0.005 | 0.02 | 0.04 |
| ORN | 80.90 | 23.67 | 83.07 | 23.25 | 78.74 | 23.96 | 0.88 | 0.29 | 0.46 |
| CIT | 38.76 | 11.40 | 39.74 | 11.95 | 37.78 | 10.77 | 0.21 | 0.66 | 0.86 |
| ARG | 72.73 | 22.56 | 71.66 | 24.54 | 73.80 | 20.42 | 0.20 | 0.09 | 0.14 |
| Acylcarnitines | | | | | | | | | |
| C2 | 9.743 | 4.481 | 10.726 | 4.863 | 8.756 | 3.834 | <.0001 | <.0001 | <.0001 |
| C3 | 0.439 | 0.230 | 0.525 | 0.253 | 0.352 | 0.164 | <.0001 | <.0001 | <.0001 |
| C4:C14 | 0.209 | 0.114 | 0.222 | 0.115 | 0.197 | 0.112 | 0.05 | 0.15 | 0.13 |
| C5:1 | 0.072 | 0.030 | 0.058 | 0.023 | 0.087 | 0.025 | <.0001 | <.0001 | <.0001 |
| C5 | 0.097 | 0.045 | 0.092 | 0.045 | 0.101 | 0.044 | 0.05 | 0.004 | 0.003 |
| C4:OH | 0.068 | 0.046 | 0.060 | 0.038 | 0.975 | 0.051 | 0.006 | 0.11 | 0.27 |
| C14-DC:C4DC | 0.056 | 0.034 | 0.065 | 0.042 | 0.048 | 0.019 | <.0001 | <.0001 | <.0001 |
| C8:1 | 0.267 | 0.137 | 0.254 | 0.126 | 0.279 | 0.145 | 0.25 | 0.53 | 0.55 |
| C8 | 0.126 | 0.113 | 0.129 | 0.121 | 0.124 | 0.106 | 0.54 | 0.17 | 0.08 |
| C5-DC | 0.042 | 0.025 | 0.044 | 0.031 | 0.040 | 0.019 | 0.29 | 0.85 | 0.43 |
| C6-DC | 0.053 | 0.080 | 0.094 | 0.101 | 0.552 | 0.049 | 0.48 | 0.62 | 0.29 |
| C10:3 | 0.139 | 0.062 | 0.144 | 0.099 | 0.133 | 0.074 | 0.67 | 0.46 | 0.61 |
| C10:1 | 0.199 | 0.096 | 0.200 | 0.099 | 0.198 | 0.096 | 0.87 | 0.47 | 0.33 |
| C10 | 0.272 | 0.267 | 0.280 | 0.307 | 0.264 | 0.220 | 0.61 | 0.94 | 0.49 |
| C10-OH:C8DC | 0.034 | 0.021 | 0.036 | 0.024 | 0.032 | 0.017 | 0.15 | 0.12 | 0.05 |
| C12:1 | 0.124 | 0.059 | 0.125 | 0.062 | 0.123 | 0.055 | 0.93 | 0.66 | 0.21 |
| C12 | 0.079 | 0.052 | 0.066 | 0.065 | 0.071 | 0.033 | 0.003 | 0.002 | 0.0005 |
| C12-OH:C10DC | 0.008 | 0.006 | 0.008 | 0.005 | 0.009 | 0.086 | 0.05 | 0.11 | 0.20 |
| C14:2 | 0.045 | 0.025 | 0.043 | 0.025 | 0.048 | 0.025 | 0.06 | 0.42 | 0.51 |
| C14:1 | 0.087 | 0.052 | 0.084 | 0.054 | 0.090 | 0.050 | 0.12 | 0.53 | 0.81 |
| C14:1-OH | 0.015 | 0.006 | 0.013 | 0.005 | 0.016 | 0.007 | 0.002 | 0.006 | 0.005 |
| C14-OH/C12-DC | 0.011 | 0.005 | 0.010 | 0.006 | 0.011 | 0.005 | 0.30 | 0.58 | 0.53 |
| C16 | 0.088 | 0.031 | 0.089 | 0.037 | 0.066 | 0.022 | 0.85 | 0.99 | 0.20 |
| C16-OH/C14-DC | 0.007 | 0.006 | 0.006 | 0.006 | 0.005 | 0.007 | 0.006 | 0.07 | 0.10 |
| C18:2 | 0.074 | 0.040 | 0.072 | 0.048 | 0.077 | 0.031 | 0.05 | 0.05 | 0.005 |
| C18:1 | 0.160 | 0.089 | 0.157 | 0.108 | 0.163 | 0.064 | 0.15 | 0.24 | 0.05 |
| C18 | 0.046 | 0.022 | 0.845 | 0.027 | 0.047 | 0.013 | 0.03 | 0.02 | <.0001 |
| C18:1-OH/C16:1-DC | 0.009 | 0.005 | 0.008 | 0.005 | 0.010 | 0.005 | 0.0055 | 0.01 | 0.02 |
| C18-OH/C16-DC | 0.003 | 0.005 | 0.008 | 0.005 | 0.009 | 0.005 | 0.005 | 0.03 | 0.009 |
| C20 | 0.007 | 0.005 | 0.007 | 0.006 | 0.007 | 0.004 | 0.22 | 0.60 | 0.89 |
| C20:1-OH/C18:1-DC | 0.011 | 0.007 | 0.011 | 0.008 | 0.011 | 0.006 | 0.19 | 0.21 | 0.37 |
| C20-OH/C18-DC | 0.009 | 0.005 | 0.009 | 0.006 | 0.010 | 0.005 | 0.02 | 0.13 | 0.19 |
| C22 | 0.008 | 0.008 | 0.009 | 0.010 | 0.007 | 0.006 | 0.73 | 0.99 | 0.88 |
| C8:1-OH/C6:1-DC | 0.026 | 0.012 | 0.027 | 0.012 | 0.028 | 0.012 | 0.47 | 0.56 | 0.67 |
| C8:1-DC | 0.027 | 0.015 | 0.029 | 0.018 | 0.025 | 0.010 | 0.10 | 0.06 | 0.04 |
| C16:2 | 0.012 | 0.007 | 0.011 | 0.006 | 0.013 | 0.007 | 0.03 | 0.11 | 0.13 |
| C16:1 | 0.051 | 0.014 | 0.029 | 0.015 | 0.032 | 0.014 | 0.03 | 0.24 | 0.25 |
| C16:1-OH/C14:1-DC | 0.010 | 0.005 | 0.009 | 0.004 | 0.011 | 0.004 | 0.008 | 0.01 | 0.004 |
| C18:2-OH | 0.011 | 0.008 | 0.012 | 0.009 | 0.011 | 0.007 | 0.45 | 0.72 | 0.50 |
| C20:4 | 0.010 | 0.005 | 0.010 | 0.007 | 0.010 | 0.005 | 0.20 | 0.22 | 0.12 |
| Other | | | | | | | | | |
| Total free fatty acids | 1.16 | 0.70 | 1.22 | 0.79 | 1.10 | 0.80 | 0.26 | 0.12 | 0.09 |
| Ketones | 316.12 | 283.99 | 319.20 | 269.88 | 313.06 | 279.02 | 0.87 | 0.44 | 0.10 |
| β-hydroxybutyrate | 207.21 | 202.44 | 211.52 | 205.69 | 202.94 | 199.81 | 0.63 | 0.29 | 0.08 |

*adjusted for age, race, sex, diabetes, hypertension, smoking, dyslipidemia, family history of CAD, BMI.
†adjusted for age, race, sex, diabetes, hypertension, smoking, dyslipidemia, family history of CAD, BMI, and total, LDL, HDL cholesterol and triglycerides.

Unbiased Principal Components Analysis

PCA identified 12 factors comprised of collinear metabolites (Table 9), grouping in biologically plausible factors. Three factors were significantly different between cases and controls in the initial group in adjusted analyses: factor 1 (medium-chain acylcarnitines), factor 4 (branched-chain amino acids and related metabolites), and factor 9 (arginine, histidine, citrulline, Ci4-DC:C4DC). Of these factors, two factors (4 and 9) remained significant in the replication group. Factor 1 was only weakly significant in the replication group (unadjusted P=0.15, adjusted P=0.03). The factor load for each metabolite is presented in Table 10.

TABLE 9

Principal Components Analysis. Results of unbiased principal components analysis (PCA) are presented. Factors were constructed using the initial group; scoring coefficients from this PCA were used to calculate factor scores for the initial and replication groups. P-values for the difference in the mean value of the factors between cases and controls for the initial and replication groups are presented.

| Factor | Name | Individual Components* | Eigen-value | Var** | Initial Group CAD Unadj | Initial Group CAD Adj† | Initial Group MI Unadj | Initial Group MI Adj† | Replication Group CAD Unadj | Replication Group CAD Adj† | Replication Group MI Unadj | Replication Group MI Adj† |
|---|---|---|---|---|---|---|---|---|---|---|---|---|
| 1 | Medium Chain Acyl-carnitines | C8, C10:1, C12, C10, C12:1, C10-OH:C8DC, C6-DC, C8:1-DC, C14:1, C14:2, C8:1-OH/C6:1-DC, C2 acylcarnitines | 12.45 | 0.21 | 0.001 | 0.01 | 0.01 | 0.06 | 0.15 | 0.03 | 0.59 | 0.18 |
| 2 | Long Chain Acyl-carnitines | C18:1, C18:2, C18, C16, C16:1, C20:4, C14:1, C14:2, C16:2, C14:1-OH | 5.78 | 0.10 | 0.28 | 0.34 | 0.21 | 0.14 | 0.03 | 0.01 | 0.08 | 0.05 |
| 3 | Long Chain Dicarboxyl/Hydroxyl Acyl-carnitines | C18-OH/C16-DC, C20-OH/C18-DC, C20:1-OH/C18:1-DC, C16-OH/C14-DC, C18:1-OH/C16:1-DC, C14-OH/C12-DC, C12-OH:C10-DC, C14:1-OH, C20 | 4.75 | 0.08 | 0.10 | 0.36 | 0.04 | 0.13 | <0.0001 | 0.004 | 0.03 | 0.21 |
| 4 | BCAA Related | Phe, Tyr, leu/Ile, Met, Val, C5, Ala | 2.87 | 0.05 | 0.002 | 0.02 | 0.0002 | 0.01 | 0.01 | 0.03 | 0.006 | 0.005 |
| 5 | Ketone Related | Ket, Hbut, Ala (−), C2, C4:OH, C14:1 | 2.24 | 0.04 | 0.18 | 0.33 | 0.02 | 0.12 | 0.54 | 0.41 | 0.07 | 0.06 |
| 6 | Various | C8:1, C10:3 | 1.92 | 0.03 | 0.56 | 0.75 | 0.92 | 0.28 | 0.79 | 0.92 | 0.76 | 0.89 |
| 7 | Amino Acids | Ser, Gly, FFA (−) | 1.71 | 0.03 | 0.19 | 0.13 | 0.59 | 0.42 | 0.04 | 0.18 | 0.28 | 0.60 |
| 8 | Dicarboxyls | C5-DC, C8:1-OH/C6:1-DC, Cit, C8:1-DC, C6-DC | 1.41 | 0.02 | 0.73 | 0.34 | 0.59 | 0.25 | 0.05 | 0.57 | 0.002 | 0.04 |

TABLE 9-continued

Principal Components Analysis. Results of unbiased principal components analysis (PCA) are presented. Factors were constructed using the initial group; scoring coefficients from this PCA were used to calculate factor scores for the initial and replication groups. P-values for the difference in the mean value of the factors between cases and controls for the initial and replication groups are presented.

| Factor | Name | Individual Components* | Eigen-value | Var** | Initial Group CAD Unadj | Initial Group CAD Adj† | Initial Group MI Unadj | Initial Group MI Adj† | Replication Group CAD Unadj | Replication Group CAD Adj† | Replication Group MI Unadj | Replication Group MI Adj† |
|---|---|---|---|---|---|---|---|---|---|---|---|---|
| 9 | Urea Cycle Related | Arg, His, Cit, Ci4-DC:C4DC (−) | 1.33 | 0.02 | 0.0004 | 0.004 | 0.0006 | 0.01 | 0.01 | 0.01 | 0.003 | 0.006 |
| 10 | Short Chain Acyl-carnitines | C3, C4:Ci4, C5 | 1.22 | 0.02 | 0.02 | 0.19 | 0.03 | 0.23 | 0.72 | 0.92 | 0.27 | 0.48 |
| 11 | Various | C5:1, C18:2-OH (−), C22 (−) | 1.15 | 0.02 | 0.62 | 0.13 | 0.95 | 0.13 | 0.03 | 0.01 | 0.13 | 0.12 |
| 12 | Various | Asx, C22 | 1.08 | 0.02 | 0.12 | 0.83 | 0.15 | 0.80 | <.0001 | <.0001 | 0.01 | 0.05 |

*Analytes with a factor load ≥|0.4| for that factor are listed, in order of magnitude of load for that factor; analytes with a negative factor load for that factor are annotated with a (−).
**Proportion of variance explained by that factor.
†adjusted for diabetes, hypertension, smoking, dyslipidemia, family history of CAD, BMI; replication group results are additionally adjusted for age, race and sex.

TABLE 10

Factor Loads of Individual Metabolites on Factors Identified from PCA on the Initial Group.

| Metabolite | 1 | 2 | 3 | 4 | 5 | 6 | 7 | 8 | 9 | 10 | 11 | 12 |
|---|---|---|---|---|---|---|---|---|---|---|---|---|
| GLY | 0.25 | 0.03 | −0.16 | 0.03 | −0.06 | 0.06 | 0.74 | 0.12 | 0.06 | −0.08 | 0.09 | 0.09 |
| ALA | 0.09 | 0.01 | 0.06 | 0.43 | −0.67 | 0.13 | 0.00 | −0.16 | 0.12 | 0.12 | 0.08 | 0.17 |
| SER | 0.01 | 0.19 | 0.02 | 0.16 | 0.07 | −0.07 | 0.76 | −0.14 | 0.17 | 0.04 | −0.06 | 0.09 |
| PRO | 0.24 | 0.02 | −0.17 | 0.36 | −0.37 | 0.12 | 0.09 | 0.17 | 0.24 | 0.06 | 0.05 | 0.37 |
| VAL | −0.24 | 0.00 | 0.02 | 0.71 | 0.07 | −0.06 | −0.12 | −0.04 | 0.06 | 0.28 | −0.11 | 0.36 |
| LEU/ILE | −0.06 | −0.05 | −0.12 | 0.79 | 0.15 | −0.06 | 0.09 | 0.00 | −0.08 | 0.30 | 0.03 | 0.19 |
| MET | 0.06 | −0.07 | 0.00 | 0.74 | −0.14 | −0.10 | 0.28 | −0.06 | 0.24 | 0.02 | 0.05 | −0.04 |
| HIS | −0.13 | 0.02 | 0.08 | 0.26 | −0.13 | −0.07 | 0.28 | −0.07 | 0.58 | 0.09 | −0.21 | −0.03 |
| PHE | −0.01 | 0.06 | 0.17 | 0.85 | −0.01 | −0.02 | −0.03 | 0.07 | 0.10 | 0.02 | −0.07 | −0.03 |
| TYR | −0.04 | 0.15 | 0.07 | 0.80 | −0.22 | 0.10 | 0.03 | −0.06 | 0.05 | −0.05 | 0.02 | −0.13 |
| ASX | −0.15 | 0.00 | 0.12 | 0.07 | 0.01 | −0.08 | 0.15 | 0.06 | 0.05 | 0.06 | 0.08 | 0.69 |
| GLX | −0.25 | 0.11 | 0.27 | 0.29 | −0.23 | 0.28 | −0.07 | 0.08 | −0.01 | 0.06 | 0.00 | 0.29 |
| ORN | 0.11 | 0.38 | −0.27 | 0.38 | −0.14 | 0.14 | 0.26 | 0.33 | −0.02 | 0.09 | −0.05 | 0.03 |
| CIT | 0.14 | 0.11 | −0.20 | 0.06 | −0.06 | 0.24 | 0.13 | 0.46 | 0.54 | −0.08 | 0.06 | 0.18 |
| ARG | −0.08 | −0.19 | −0.02 | 0.26 | −0.07 | −0.09 | 0.18 | 0.07 | 0.68 | 0.07 | 0.13 | 0.04 |
| C2 | 0.44 | 0.33 | 0.08 | 0.00 | 0.60 | 0.16 | 0.11 | −0.13 | 0.02 | 0.22 | 0.11 | 0.07 |
| C3 | 0.00 | 0.01 | −0.16 | 0.23 | −0.15 | 0.06 | 0.04 | −0.09 | 0.11 | 0.72 | 0.03 | 0.05 |
| C4:Ci4 | 0.30 | −0.06 | −0.01 | 0.19 | −0.13 | 0.14 | 0.03 | 0.18 | −0.03 | 0.50 | 0.13 | 0.01 |
| C5:1 | 0.14 | −0.05 | −0.07 | −0.03 | −0.04 | −0.09 | 0.02 | −0.05 | 0.01 | 0.30 | 0.69 | 0.10 |
| C5 | 0.13 | 0.03 | 0.04 | 0.44 | −0.06 | 0.06 | −0.14 | 0.20 | −0.01 | 0.49 | 0.02 | 0.10 |
| C4:OH | 0.32 | 0.05 | 0.07 | 0.00 | 0.56 | 0.24 | 0.23 | −0.07 | −0.19 | 0.19 | 0.29 | 0.00 |
| C14-DC:C4DC | 0.39 | −0.01 | −0.12 | 0.18 | 0.05 | 0.12 | 0.22 | 0.32 | −0.43 | 0.08 | 0.06 | −0.21 |
| C8:1 | 0.27 | 0.04 | 0.12 | 0.01 | 0.06 | 0.85 | −0.02 | 0.03 | −0.02 | 0.10 | −0.09 | 0.05 |
| C8 | 0.80 | 0.16 | 0.15 | −0.01 | 0.10 | 0.09 | 0.06 | −0.02 | 0.01 | 0.11 | −0.13 | −0.03 |
| C5-DC | 0.34 | −0.03 | 0.28 | 0.02 | −0.04 | −0.11 | −0.10 | 0.62 | 0.11 | 0.05 | −0.08 | 0.07 |
| C6-DC | 0.60 | 0.06 | 0.29 | −0.05 | 0.04 | 0.14 | −0.02 | 0.41 | −0.15 | −0.03 | 0.11 | 0.07 |
| C10:3 | 0.30 | 0.07 | 0.10 | −0.04 | 0.05 | 0.82 | 0.01 | 0.07 | −0.04 | 0.04 | −0.04 | −0.10 |
| C10:1 | 0.76 | 0.16 | 0.12 | −0.03 | 0.04 | 0.31 | 0.01 | 0.03 | 0.00 | 0.09 | −0.18 | −0.04 |
| C10 | 0.72 | 0.06 | 0.00 | −0.09 | 0.14 | −0.05 | 0.09 | −0.06 | −0.04 | 0.03 | 0.04 | 0.04 |
| C10-OH:C8DC | 0.65 | 0.16 | 0.39 | 0.00 | 0.19 | 0.14 | −0.08 | 0.22 | −0.08 | 0.03 | 0.11 | −0.01 |
| C12:1 | 0.88 | 0.26 | 0.25 | 0.10 | 0.23 | 0.23 | −0.09 | 0.10 | 0.04 | −0.06 | 0.15 | −0.11 |
| C12 | 0.74 | 0.13 | 0.00 | 0.01 | 0.02 | 0.03 | 0.12 | 0.16 | −0.06 | −0.01 | 0.24 | −0.12 |
| C12-OH:C10DC | 0.33 | 0.09 | 0.46 | −0.02 | 0.12 | 0.05 | −0.11 | 0.12 | 0.14 | −0.07 | −0.06 | 0.20 |
| C14:2 | 0.47 | 0.48 | 0.38 | 0.04 | 0.37 | 0.14 | −0.10 | 0.02 | 0.12 | −0.07 | −0.21 | 0.00 |
| C14:1 | 0.52 | 0.49 | 0.39 | 0.02 | 0.40 | 0.05 | −0.12 | −0.01 | 0.07 | −0.04 | −0.10 | 0.02 |
| C14:1-OH | 0.34 | 0.42 | 0.44 | 0.04 | 0.20 | 0.11 | 0.01 | 0.06 | 0.01 | 0.01 | −0.02 | −0.08 |
| C14-OH/C12-DC | 0.16 | 0.29 | 0.51 | 0.09 | −0.03 | 0.09 | 0.09 | −0.10 | −0.19 | 0.01 | −0.02 | 0.12 |
| C16 | 0.23 | 0.71 | 0.30 | 0.08 | 0.15 | −0.05 | 0.02 | −0.15 | −0.14 | 0.03 | 0.14 | 0.11 |
| C16-OH/C14-DC | 0.18 | 0.18 | 0.57 | −0.01 | 0.07 | 0.00 | −0.23 | −0.09 | 0.02 | 0.02 | 0.05 | 0.09 |
| C18:2 | 0.16 | 0.79 | 0.16 | 0.07 | 0.11 | 0.16 | 0.03 | 0.05 | −0.02 | −0.10 | −0.22 | 0.04 |

TABLE 10-continued

Factor Loads of Individual Metabolites on Factors Identified from PCA on the Initial Group.

| Metabolite | FACTOR | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| C18:1 | 0.22 | 0.83 | 0.24 | 0.04 | 0.19 | 0.01 | 0.06 | 0.00 | −0.08 | −0.09 | −0.03 | 0.00 |
| C18 | 0.08 | 0.75 | 0.25 | −0.07 | 0.01 | −0.02 | 0.14 | 0.01 | −0.02 | 0.08 | 0.03 | 0.01 |
| C18:1-OH/C16:1-DC | 0.15 | 0.11 | 0.52 | 0.07 | 0.19 | 0.01 | −0.07 | 0.01 | −0.01 | −0.20 | −0.17 | 0.24 |
| C18-OH/C16-DC | −0.05 | 0.19 | 0.69 | 0.06 | 0.00 | 0.09 | −0.01 | 0.08 | −0.10 | −0.03 | −0.10 | 0.09 |
| C20 | −0.04 | 0.26 | 0.42 | −0.07 | 0.05 | 0.00 | −0.15 | 0.04 | 0.34 | 0.12 | −0.07 | −0.06 |
| C20:1-OH/C18:1-DC | 0.11 | 0.24 | 0.62 | 0.01 | 0.10 | 0.12 | 0.01 | 0.15 | 0.08 | −0.06 | −0.17 | −0.12 |
| C20-OH/C18-DC | 0.15 | 0.15 | 0.62 | 0.00 | −0.01 | −0.01 | 0.14 | 0.07 | 0.03 | 0.00 | 0.05 | −0.14 |
| C22 | 0.04 | 0.03 | 0.00 | 0.06 | 0.01 | 0.05 | −0.07 | −0.03 | 0.00 | 0.03 | −0.46 | 0.41 |
| C8:1-OH/C6:1-DC | 0.46 | 0.02 | 0.12 | −0.09 | −0.11 | 0.31 | 0.02 | 0.46 | −0.03 | 0.13 | −0.06 | 0.12 |
| C8:1-DC | 0.56 | 0.08 | 0.10 | −0.03 | −0.07 | 0.30 | 0.10 | 0.44 | −0.06 | 0.01 | 0.18 | −0.09 |
| C16:2 | 0.17 | 0.47 | 0.34 | 0.09 | 0.30 | 0.05 | −0.24 | 0.03 | 0.22 | −0.11 | −0.26 | 0.03 |
| C16:1 | 0.39 | 0.62 | 0.27 | 0.00 | 0.32 | −0.03 | −0.14 | −0.09 | 0.06 | −0.17 | −0.02 | −0.07 |
| C16:1-OH/C14:1-DC | 0.22 | 0.36 | 0.32 | −0.02 | 0.19 | 0.02 | 0.02 | −0.06 | 0.18 | −0.08 | 0.23 | −0.08 |
| C18:2-OH | −0.02 | 0.24 | 0.29 | −0.06 | −0.06 | 0.00 | 0.09 | −0.03 | 0.01 | 0.17 | −0.51 | −0.08 |
| C20:4 | −0.24 | 0.58 | 0.15 | 0.07 | −0.13 | 0.06 | 0.03 | 0.22 | 0.02 | 0.16 | −0.25 | −0.01 |
| FFA | 0.10 | 0.23 | −0.13 | 0.05 | 0.19 | −0.01 | −0.44 | −0.36 | −0.22 | −0.33 | 0.02 | 0.22 |
| HBUT | 0.17 | 0.24 | 0.15 | −0.05 | 0.85 | 0.02 | −0.09 | −0.08 | −0.03 | −0.22 | −0.04 | 0.05 |
| KET | 0.17 | 0.20 | 0.15 | −0.04 | 0.87 | 0.01 | −0.07 | −0.06 | −0.03 | −0.20 | −0.01 | 0.04 |

Further adjustment for lipids showed continued association with CAD, although Factor 4 was not significant in the initial group (initial group: factor 1, P=0.0002; factor 4, P=0.59; factor 9, P=0.02; replication group: factor 1, P=0.01; factor 4, P=0.02; factor 9, P=0.004). Although we adjusted for diabetes, given studies showing relationships between metabolites with insulin resistance, we further adjusted the base multivariable model for fasting glucose. These analyses revealed a continued significant association with CAD (initial group: factor 1, P=0.02; factor 4, P=0.02; factor 9, P=0.003; replication group: factor 1, P=0.03; factor 4, P=0.05; factor 9, P=0.02).

Stratified analyses suggested stronger association between factors 4 and 9 with CAD in non-diabetics as compared with diabetics (Table 11), with minimal or no discernable signal in diabetics, but no consistent differences in association with CAD by smoking (Table 12).

TABLE 11

Association of PCA Derived Metabolomic Factors with CAD, Stratified by Diabetes. P-values for the association of PCA-derived metabolomic factors with CAD, stratified by a medical history of diabetes, are presented. Unadjusted p-values and p-values adjusted for hypertension, smoking, dyslipidemia, family history and BMI (and also for age, race and sex in the Replication Group) are presented.

| | | Initial Group | | | | Replication Group | | | |
|---|---|---|---|---|---|---|---|---|---|
| | | Diabetics | | Non-Diabetics | | Diabetics | | Non-Diabetics | |
| Factor | Name | Unadj | Adj | Unadj | Adj | Unadj | Adj | Unadj | Adj |
| 1 | Medium Chain Acylcarnitines | 0.007 | 0.01 | 0.03 | 0.19 | 0.15 | 0.09 | 0.42 | 0.26 |
| 2 | Long Chain Acylcarnitines | 0.70 | 0.65 | 0.12 | 0.46 | 0.06 | 0.08 | 0.23 | 0.15 |
| 3 | Long Chain Dicarboxyl/Hydroxyl Acylcarnitines | 0.85 | 0.77 | 0.04 | 0.18 | 0.53 | 0.54 | <0.0001 | 0.002 |
| 4 | BCAA Related | 0.12 | 0.09 | <0.0001 | 0.0003 | 0.86 | 0.75 | 0.005 | 0.0004 |
| 5 | Ketone Related | 0.06 | 0.11 | 0.56 | 0.97 | 0.13 | 0.23 | 0.95 | 0.94 |
| 6 | Various | 0.01 | 0.07 | 0.17 | 0.10 | 0.33 | 0.88 | 0.25 | 0.69 |
| 7 | Amino Acids | 0.41 | 0.32 | 0.38 | 0.27 | 0.61 | 0.69 | 0.03 | 0.08 |
| 8 | Dicarboxyis | 0.18 | 0.11 | 0.76 | 0.82 | 0.80 | 0.88 | 0.06 | 0.28 |
| 9 | Urea Cycle Related | 0.69 | 0.98 | 0.0005 | 0.0002 | 0.53 | 0.44 | 0.02 | 0.002 |
| 10 | Short Chain Acylcarnitines | 0.09 | 0.25 | 0.16 | 0.35 | 0.90 | 0.87 | 0.89 | 0.85 |
| 11 | Various | 0.14 | 0.14 | 0.99 | 0.27 | 0.19 | 0.04 | 0.08 | 0.19 |
| 12 | Various | 0.11 | 0.10 | 0.61 | 0.52 | 0.06 | 0.11 | <0.0001 | <0.0001 |

TABLE 12

Association of PCA Derived Metabolomic Factors with CAD, Stratified by Smoking. P-values for the association of PCA-derived metabolomic factors with CAD, stratified by smoking (currently smoking or not), are presented. Unadjusted p-values and p-values adjusted for diabetes, hypertension, dyslipidemia, family history and BMI (and also for age, race and sex for the Replication Group) are presented.

| | | Initial Group | | | | Replication Group | | | |
| | | Smokers | | NonSmokers | | Smokers | | Non-Smokers | |
| Factor | Name | Unadj | Adj | Unadj | Adj | Unadj | Adj | Unadj | Adj |
| --- | --- | --- | --- | --- | --- | --- | --- | --- | --- |
| 1 | Medium Chain Acylcarnitines | 0.03 | 0.09 | 0.009 | 0.05 | 0.38 | 0.18 | 0.14 | 0.16 |
| 2 | Long Chain Acylcarnitines | 0.15 | 0.05 | 0.87 | 0.64 | 0.24 | 0.15 | 0.04 | 0.07 |
| 3 | Long Chain Dicarboxyl/Hydroxyl Acylcarnitines | 0.08 | 0.33 | 0.77 | 0.81 | 0.48 | 0.50 | <0.0001 | 0.0005 |
| 4 | BCAA Related | 0.003 | 0.07 | 0.24 | 0.23 | 0.27 | 0.12 | 0.02 | 0.005 |
| 5 | Ketone Related | 0.14 | 0.84 | 0.76 | 0.46 | 0.24 | 0.71 | 0.83 | 0.70 |
| 6 | Various | 0.82 | 0.32 | 0.46 | 0.62 | 0.89 | 0.87 | 0.96 | 0.77 |
| 7 | Amino Acids | 0.16 | 0.18 | 0.69 | 0.41 | 0.02 | 0.10 | 0.84 | 0.79 |
| 8 | Dicarboxyls | 0.39 | 0.12 | 0.42 | 0.79 | 0.66 | 0.90 | 0.05 | 0.16 |
| 9 | Urea Cycle Related | 0.14 | 0.58 | 0.0001 | 0.0004 | 0.04 | 0.05 | 0.02 | 0.03 |
| 10 | Short Chain Acylcarnitines | 0.14 | 0.41 | 0.08 | 0.27 | 0.37 | 0.39 | 0.48 | 0.58 |
| 11 | Various | 0.83 | 0.94 | 0.40 | 0.08 | 0.23 | 0.11 | 0.07 | 0.15 |
| 12 | Various | 0.15 | 0.47 | 0.97 | 0.60 | 0.0004 | 0.002 | 0.0002 | 0.0001 |

Additional adjustment for ten classes of medications had minimal influence on the relationship between factors and CAD in the initial group (factor 1, adjusted P=0.009; factor 4, P=0.03; factor 9, P=0.003), but were no longer significant in the replication group (factor 1, P=0.02; factor 4, P=0.19; factor 9, P=0.14). We also performed similar analyses restricted to those individuals with available medication data, in the combined datasets to optimize power (N=416). These results showed continued association between factors 4 and 9 with CAD, although attenuated (factor 4: unadjusted model, p=0.0009; model adjusted for CAD risk factors, P=0.03; model adjusted for CAD risk factors and medications, P=0.05; factor 9: unadjusted model, P=0.0003; model adjusted for CAD risk factors, P=0.002; model adjusted for CAD risk factors and medications, P=0.007).

Results presented are unadjusted for multiple comparisons. We used PCA to account for co-linearity of metabolites. Of the individual metabolites, only glutamate/glutamine would survive Bonferroni correction. Factors 4 and 9 would survive Bonferroni correction at the level of factors (P<0.004).

Association of Metabolite Profiles with Prevalent Myocardial Infarction

To examine association of these metabolites with a more severe phenotype, we evaluated the relationship of the PCA-derived factors in cases with a prior history of MI compared with controls free of CAD (initial group N=86 MI cases, replication group N=61 MI case). The two factors (4 and 9) that were associated with CAD were also associated with prior MI in both groups (Table 9).

Assessment of Model Fit and ROC Curves for CAD

To further quantify the independent association of metabolite factors with CAD, logistic regression models were constructed: (1) clinical model; (2) clinical model plus factors 4 and 9; and (3) clinical model plus all metabolite factors. Factors 4 and 9 were independently associated with CAD in both the initial group (factor 4: odds ratio [OR] 1.42; 95% CI, 1.09 to 1.84, P=0.01; factor 9: OR 0.69, 95% CI, 0.53 to 0.90, P=0.006) and the replication group (factor 4: OR 1.42; 95% CI 1.06 to 1.89, P=0.02; factor 9: OR 0.67; 95% CI 0.48 to 0.92, P=0.01). Measure of model fit and ROC curves (FIG. 1) in the initial group showed modestly greater discriminative capability for models containing factors 4 and 9 (c-statistic 0.778), with some improvement with addition of all factors (c-statistic 0.804), above the model containing only clinical variables (c-statistic 0.756; P=0.06 for comparison of clinical model to clinical model plus factors 4 and 9; P=0.003 for comparison of clinical model to clinical model plus all factors). In the replication group, there was a slightly higher c-statistic with the addition of factors 4 and 9 to the clinical model (c-statistic 0.773) than for the clinical model alone (c-statistic 0.743), but more dramatic improvement with addition of all factors (c-statistic 0.874; P=0.04 for comparison of clinical model to clinical model plus factors 4 and 9; and P<0.0001 for comparison of clinical model to clinical model plus all factors).

Given it is standard of care to measure lipids in patients in whom a diagnosis of CAD is being considered, and that CRP is a recognized biomarker of cardiovascular disease, we reconstructed these models including lipids and CRP. These analyses revealed a higher clinical model fit in both initial and replication groups (c-statistic 0.842 and 0.778, respectively). The addition of factors 4 and 9 to the clinical model inclusive of lipids and CRP resulted in no improvement in the discriminative ability of the model in the initial group (c-statistic 0.848, P=0.31 for comparison with clinical model), with some improvement with addition of all factors (c-statistic 0.865, P=0.01 for comparison with clinical model). However, the magnitude of improvement in the clinical model with addition of metabolite factors remained similar and large in the replication group (c-statistics: clinical model inclusive of lipids and CRP, 0.778; clinical model+factors 4 and 9, 0.799, P=0.08; clinical model+all metabolite factors, 0.900, P=0.0001 for comparison with clinical model).

Metabolite Factors and Risk of Subsequent Cardiovascular Events

Figure 2:
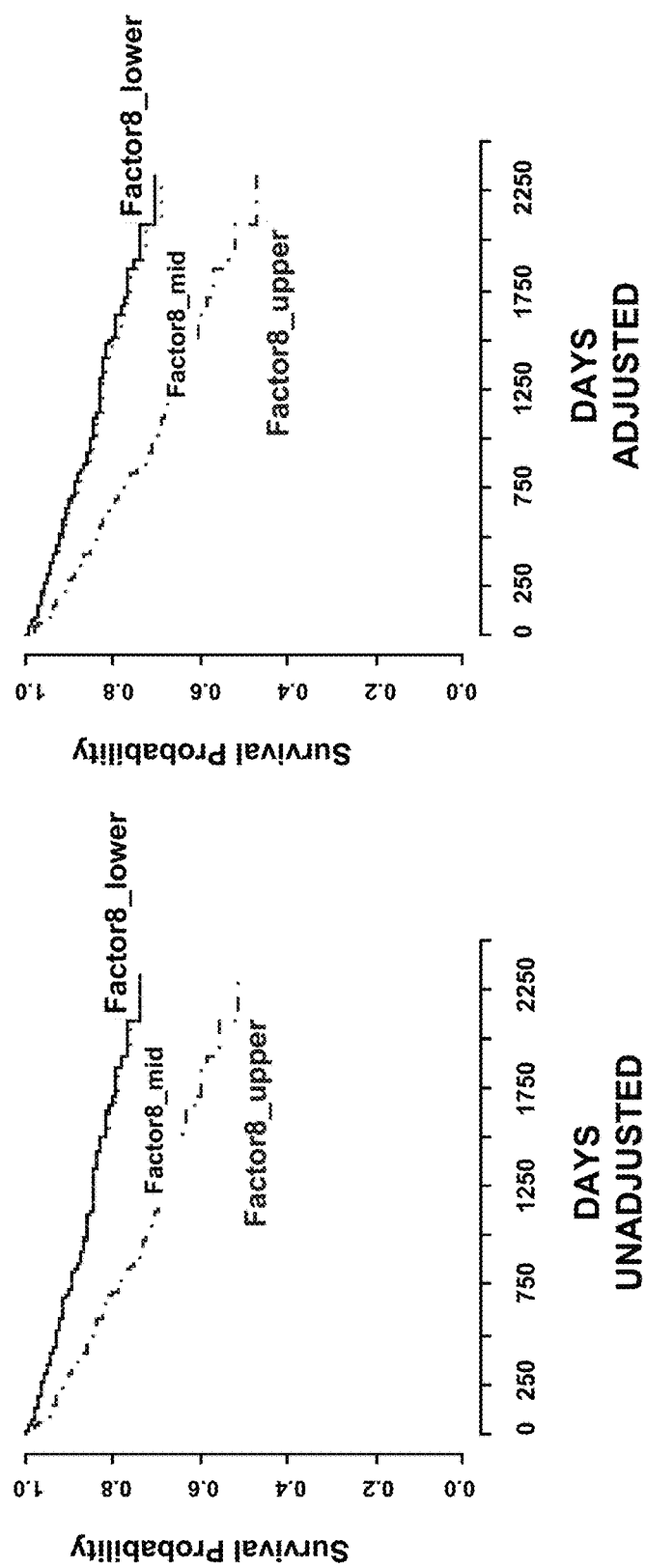
FIG. 2 is a set of graphs showing the cox proportional hazards model for predictive capability of metabolite Factor 8 for cardiovascular events. Unadjusted (left panel) and adjusted (right panel) survival curves (adjusted for BMI, severity of CAD, hypertension, dyslipidemia, diabetes, smoking, family history, ejection fraction, serum creatinine, subsequent CABG, age, race and sex) are presented for metabolite factor 8.

During a median of 2.72 years of follow-up, 74 of 314 CAD cases had an incident cardiovascular event. In unadjusted comparisons, factor 8 (short-chain dicarboxylacylcarnitines) was highly associated with occurrence of death or MI (FIG. 2; highest versus lowest tertile hazard ratio [HR] 2.50; 95% CI, 1.47 to 4.17; P=0.0008; highest versus middle tertile HR 2.33; 95% CI, 1.39 to 3.85; P=0.002). The strength of this association was somewhat attenuated after adjustment for CAD risk factors, CADindex, age, race, sex, ejection fraction, creatinine and treatment with CABG after catheterization (highest versus lowest tertile: HR 1.67; 95% CI, 0.88 to 3.13; P=0.11; highest versus middle tertile: HR 1.89; 95% CI 1.09 to 3.33; P=0.03). Factor 1 was also associated with the occurrence of death/MI in unadjusted comparisons (highest versus lowest tertile HR 1.85; 95% CI, 1.06 to 3.23; P=0.03; highest versus middle tertile HR 1.79; 95% CI, 1.02 to 3.03; P=0.04), but was no longer significant after adjustment (P=0.14 and 0.05, respectively).

To validate these findings, we performed metabolomic profiling in an independent case-control dataset ('event-replication' group). In this group, factor 8 was associated with cardiovascular events (unadjusted OR 1.52; 95% CI, 1.08 to 2.14; P=0.01; adjusted OR 1.82; 95% CI, 1.08 to 3.50; P=0.03), with higher scores in cases who suffered subsequent cardiovascular events versus event-free controls. Individual metabolites within the factor were also significantly different (P<0.05) between cases and controls, with a similar direction of effect as observed in the original 'event' dataset.

This example demonstrates that peripheral blood metabolite profiles are independently associated with the presence of CAD, and add to the discriminative capability for CAD compared with models containing only clinical variables. Further, we report a specific metabolite cluster that independently predicts subsequent cardiovascular events in individuals with CAD.

Example 2: Heritability of CAD

Materials and Methods
Study Population.

Figure 3:
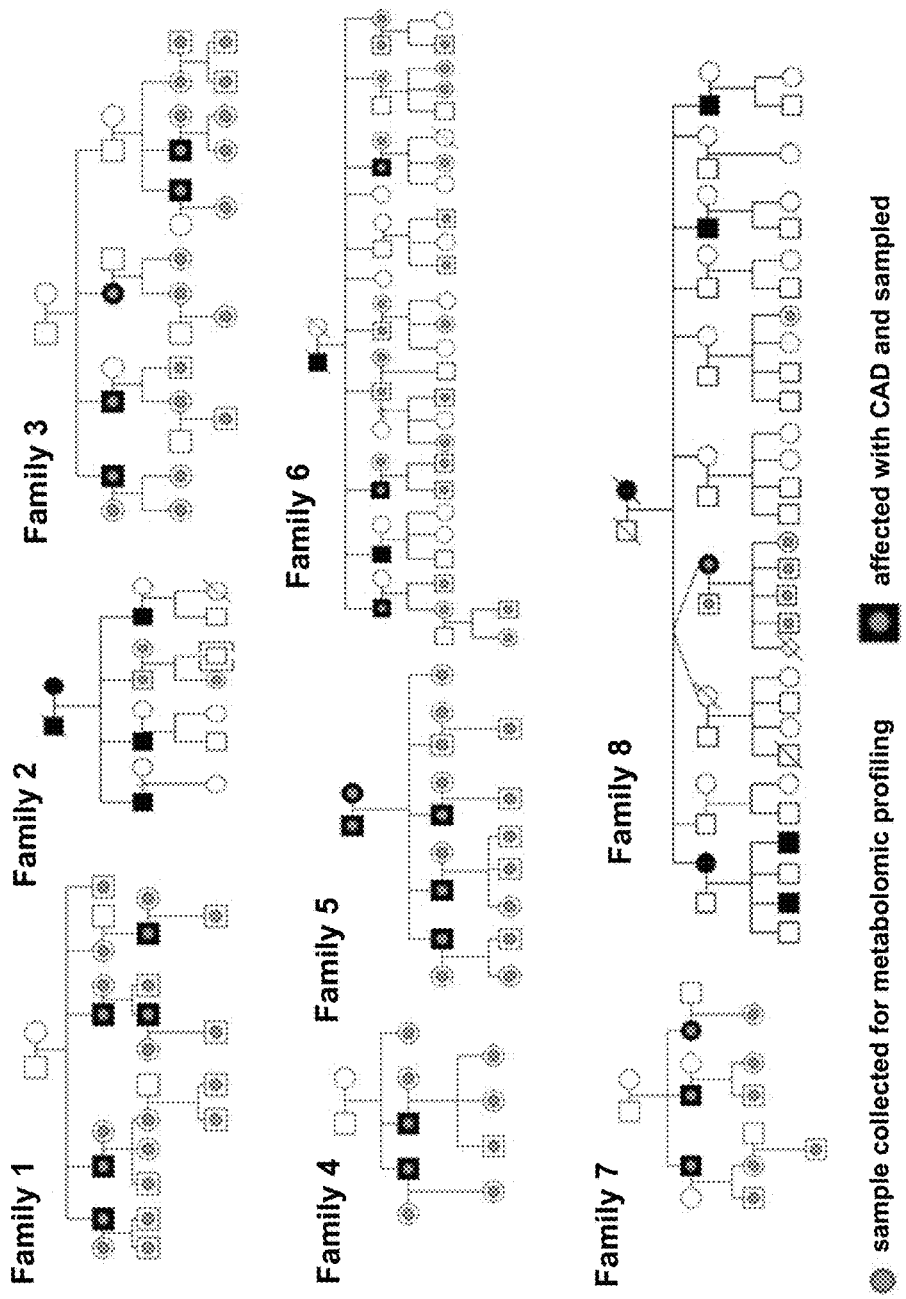
FIG. 3 is a pedigree of the eight multiplex GENECARD families. Black filled in symbols signify affected with premature CAD; smaller gray circles signify blood profiling performed for this study. Note that the majority of the family members profiled are as-of-yet unaffected offspring of the original affected-sibling pairs.

The GENECARD study enrolled 920 families to perform affected-sibling-pair linkage for identification of genes for early-onset CAD (before age 51 for men, age 56 for women) (Hauser et al., 2003, Am Heart J, 145, 602-613). Families with at least two siblings each of whom met the criteria for early-onset CAD (before age 51 for men, age 56 for women) were recruited. Unaffected family members were defined as no clinical evidence of CAD and age greater than 55 years for men (greater than 60 years for women). From this cohort, we selected eight representative families we believed would be particularly informative, based on availability of a relatively large number of family members and a heavy burden of CAD in the proband and surrounding generations (FIG. 3). These families were recontacted; the affected-sibling-pair and family members not previously enrolled were ascertained regardless of CAD, focused on offspring of the affected-sibling-pair. This ascertainment strategy was based on the hypothesis that if abnormalities in metabolic profiles preceded development of CAD in these families, that significant concordance of metabolite levels within families would be evident even in the absence of overt CAD in the offspring. Sample collections within a given family were done at several different times and at different locations, by a single experienced phlebotomist. Blood samples were promptly processed after collection via peripheral venous phlebotomy (within minutes), frozen as soon as possible thereafter (at most within 12 hours with the majority of samples being frozen within 1-2 hours of collection), and stored as plasma samples in EDTA-treated tubes at −80° C. Samples were collected as often as possible in a fasting state; however, the consistency of this could not be determined. Institutional Review Boards approved study protocols; informed consent was obtained from each subject.

Biochemical Measurements.

Frozen plasma samples were used to quantitatively measure targeted metabolites, including 37 acylcarnitine species, 15 amino acids, nine free fatty acids and conventional analytes, ketones and C-reactive protein (CRP). Sample preparation and coefficients of variation have been reported (Haqq et al., 2005 Contemp Clin Trials, 26, 616-625). The laboratory was blinded to family identifiers and case-control status. Assay ranges are 0.05-40 micromolar (μM) (acylcarnitines); 5-1000 μM (amino acids); and 1-1000 mmol/L (fatty acids). For simplicity, the clinical shorthand of metabolites is used (Table 1). Intra-individual variability was assessed in samples from five individuals for which repeat profiling was performed on the same sample on five separate days. Coefficients-of-variation and correlation confirmed minimal inter-assay variability (Table 1).

Conventional Metabolite Analysis.

Standard clinical chemistry methods were used for conventional metabolites, including glucose, total cholesterol, high-density-lipoprotein (HDL)- and low-density-lipoprotein (LDL) cholesterol, and triglycerides with reagents from Roche Diagnostics (Indianapolis, Ind.); and free fatty acids (total) and ketones (total and 3-hydroxybutyrate) with reagents from Wako (Richmond, Va.). All measurements were performed using a Hitachi 911 clinical chemistry analyzer.

Acylcarnitines and Amino Acids.

Proteins were first removed by precipitation with methanol. Aliquoted supernatants were dried, and then esterified with hot, acidic methanol (acylcarnitines) or n-butanol (amino acids). Acylcarnitines and amino acids were analyzed by tandem MS with a Quattro Micro instrument (Waters Corporation, Milford, Mass.). Thirty-seven acylcarnitine species and 15 amino acids in plasma were assayed by our previously described methods (Millington et al., 1990, J Inherit Metab Dis, 13, 321-324; An et al., 2004, Nat Med, 10, 268-274; Wu et al., 2004, J Clin Invest, 113, 434-440). Leucine/isoleucine (LEU/ILE) are reported as a single analyte because they are not resolved by our MS/MS method, and include contributions from alto-isoleucine and hydroxyproline. Under normal circumstances these isobaric amino acids contribute little to the signal attributed to LEU/ILE. In addition, the acidic conditions used to form butyl esters results in partial hydrolysis of glutamine to glutamic acid and of asparagine to aspartate. Accordingly, values that are reported as GLU/GLN or ASP/ASN are not meant to signify the molar sum of glutamate and glutamine, or of aspartate and asparagine, but rather measure the amount of glutamate or aspartate plus the contribution of the partial hydrolysis reactions of glutamine and asparagine, respectively.

Free Fatty Acids.

Free fatty acids were gently methylated using iodomethane and purified by solid-phase extraction (Patterson et al., 1999, J Lipid Res, 40, 2118-2124). Derivatized fatty acids were analyzed by capillary gas chromatography/mass spectrometry (GC/MS) using a Trace DSQ instrument (Thermo Electron Corporation, Austin, Tex.). Due to sample volume considerations, only 80 of the 117 individuals (five out of eight families) had free fatty acid measurements performed.

All mass-spectrometric analyses employed stable-isotope-dilution. Quantification of the foregoing "targeted" intermediary metabolites was facilitated by addition of mixtures of known quantities of stable-isotope internal standards to samples, from Isotec (St. Louis, Mo.), Cambridge Isotope Laboratories (Andover, Mass.) and CDN Isotopes (Pointe-Claire, Quebec, CN) (Table 3).

Heritability Analysis.

Heritabilities were calculated using the Sequential Oligogenic Linkage Analysis Routines (SOLAR) software version 4.0.7 (Almasy and Blangero, 1998, Am J Hum Genet, 62, 1198-1211), which uses maximum-likelihood methods to estimate variance components, allowing incorporation of fixed effects for known covariates and variance components for genetic effects. This approach appropriately accounts for correlation between all family members and allows incorporation of extended pedigrees such as is present in the current study. The total variation is partitioned into components for additive genetic variance and environmental variance, as well as a residual (unexplained) variability. The program uses the pedigree covariance matrix $$\Omega = 2\Phi\sigma_s^2 + I\sigma_s^2$$

where $\Omega$ is the covariance matrix, $\Phi$ is the matrix of kinship values, $i\sigma_s^2$ is the additive genetic variance, I represents the identity matrix, and $\sigma_s^2$ is the random environmental variance (Almasy et al., 1998, supra). This model allows for complex pedigree data (i.e. beyond parent-offspring pairs) and hence, the resulting heritability estimates are more accurate than those obtained using only nuclear family members. For the current study, all sampled individuals from the pedigree were entered into the variance components models, including unaffected offspring, cousins, and married-in family members. Incorporation of married-in family members (i.e. genetically unrelated but with shared environment) allows for better estimation of the environmental component of intrafamilial clustering of traits.

Values considered outliers were excluded from heritability analyses, defined as values falling outside of the mean±4SD (one-two outliers for each of 24 of the metabolites). Metabolite measurements below the lower limits of quantification (LOQ) were given a value of LOQ/2. Four metabolites having >25% of samples below LOQ were not further analyzed (C6, C5-OH:C3-DC, C4DC, and C10:2 acylcarnitines). All measurements were natural log-transformed prior to analysis, resulting in most metabolites approximating a normal distribution, an important consideration for variance components analysis. Eighteen metabolites did not meet this criterion, and therefore, linear regression models adjusted for body-mass index (BMI), age, sex, CAD, diabetes mellitus (DM (yes/no), hypertension (yes/no), and dyslipidemia (yes/no) were constructed for each of these metabolites, and the residuals were used for heritability estimates. Given occasional low trait standard deviations for metabolites (<0.5), all log transformed metabolites were multiplied by a factor of 4.7 prior to analysis.

Polygenic heritability models were then constructed. For the normally distributed metabolites (the majority of metabolites), polygenic heritability models were calculated using the log-transformed values, adjusting for age, sex, BM1, DM, dyslipidemia, hypertension and CAD. The proband and family members were not selected based on any metabolite values; however, the potential for ascertainment bias exists. Therefore, analyses were corrected based on which of the family members (proband) was the index member for ascertainment of the family for early-onset CAD. To account for factors such as diet (which are shared in households but are presumably not genetic) an additional variance component parameter corresponding to the fraction of variance associated with the effect of a common household (included in the model by a marker for residential address), was added to each model. All residual kurtoses for the final polygenic model were within normal range (i.e. <0.8), except for two amino acids (serine and phenylalanine), eleven acylcarnitines (C5, C10, C10:1, C10:3, C12:1, C14, C14-OH:C12-DC, C16-OH:C14-DC, C18:1-OH, C18:1-DC, and C18-DC:C20-OH) and three free fatty acids (FAC14:0, FAC16:1, FAC18:1). For these metabolites, removal of 1-4 of the most extreme values was necessary, which then resulted in a normal residual kurtosis. Two acylcarnitines required removal of a larger number of outliers to achieve a normal residual kurtosis (C16-OH:C14-DC and C12-OH:C10-DC), and hence, these results should be interpreted accordingly. For the eighteen non-normally distributed metabolites, standardized residuals from adjusted regression models were used to estimate heritabilities using SOLAR, but since the normalized deviates were already adjusted for relevant covariates heritability models using these residuals were not further adjusted. Estimates of the proportion of variance explained by clinical covariates are reported for these non-normally distributed metabolites as estimated using the adjusted polygenic model constructed from the log-transformed crude values.

For understanding quantitative differences in metabolites between families, multivariable generalized linear models adjusted for sex, age, BMI, CAD, DM, dyslipidemia and hypertension, were used to compare mean metabolite levels between families.

Unsupervised Principal Components Analyses.

Given that many metabolites reside in overlapping pathways, correlation of metabolites is expected. To understand the correlation, we used principal components analysis (PCA) to reduce the large number of correlated variables into clusters of fewer uncorrelated factors using raw metabolite values without removal of outliers. The factor with the highest "eigenvalue" accounts for the largest amount of the variability within the dataset. Standardized residuals calculated for each metabolite from linear regression models adjusted for age, sex, BMI, DM, and CAD, were used as input for PCA. PCA using residuals is recommended when, as in this case, the units for each variable vary significantly in magnitude (Johnson and Wichem D. W., 1988, *Applied Multivariate Statistical Analysis*. Prentice Hall, Englewood Cliffs, N.J.). Factors with an eigenvalue $\geq 1.0$ were identified based on the commonly employed Kaiser criterion (Kaiser, 1960, *Educational and Psychological Measurement*, 20, 141-151). Varimax rotation was then performed to produce interpretable factors. Metabolites with a factor load $\geq |0.4|$ are reported as composing a given factor, as is commonly used as an arbitrary threshold (Lawlor et al., 2004, *Am J Epidemiol*, 159, 1013-1018). Scoring coefficients were then used to compute factor scores for each individual (consisting of a weighted sum of the values of the standardized metabolites within that factor, weighted on the factor loading calculated for each individual metabolite). These factor scores were then used to calculate heritabilities for each factor with SOLAR as detailed above, using a polygenic model not further adjusted for covariables. Removal of 1-4 of the most extreme values for several of the factors was necessary to achieve a normal residual kurtosis.

As all analyses were exploratory in nature and given collinearity of the metabolites, nominal two-sided p-values unadjusted for multiple comparisons are presented, however results interpreted in the context of a conservative Bonferroni correction are reported. Nominal statistical significance was defined as p-value<0.05. Statistical analyses used SAS version 9.1 (SAS Institute, Cary N.C.), other than for heritability estimates which used SOLAR (Almasy et al., 1998, supra).

Results and Discussion

Heritability Analysis.

Metabolic profiling was performed on 117 individuals within eight multiplex Caucasian families (FIG. 3) from the GENECARD study of premature CAD. Of note, the majority of family members sampled for this study were as-yet-unaffected offspring of the original affected-sibling-pair, but who, as members of these families, were at high risk for development of premature CAD. As expected, there was a high burden of CAD risk factors, although the prevalence differed between families (Table 13).

TABLE 13

Clinical characteristics of GENECARD families. The overall baseline clinical characteristics of the GENECARD cohort are presented, as well as baseline characteristics within each family.

| Variable | Overall (N = 117) | Family 1 (N = 22) | Family 2 (N = 3) | Family 3 (N = 22) | Family 4 (N = 9) | Family 5 (N = 18) | Family 6 (N = 27) | Family 7 (N = 9) | Family 8 (N = 7) |
|---|---|---|---|---|---|---|---|---|---|
| Age (SD) | 45.62 (15.82) | 49.77 (16.12) | 39.00 (18.25) | 39.27 (15.85) | 49.22 (11.12) | 49.33 (17.82) | 44.04 (15.38) | 46.33 (15.00) | 49.29 (15.96) |
| Sex (% female) | 48.7% | 36.4% | 66.7% | 59.1% | 66.7% | 44.4% | 48.2% | 44.4% | 42.9% |
| Diabetes (%) | 9.4% | 13.6% | 0.0% | 9.1% | 22.2% | 16.7 | 0.0% | 11.1% | 0.0% |
| Hypertension (%) | 36.8% | 36.4% | 66.7% | 36.4% | 33.3% | 44.4% | 22.2 | 33.3% | 71.4% |
| Dyslipidemia (%) | 35.0% | 45.5% | 0.0% | 31.8% | 44.4% | 44.4% | 22.2 | 44.4% | 28.6% |
| BMI (SD) | 28.68 (5.70) | 28.77 (5.86) | 32.02 (7.13) | 26.73 (5.90) | 35.59 (7.18) | 30.19 (5.38) | 27.43 (4.05) | 27.98 (3.30) | 25.81 (4.00) |
| Total cholesterol mean (SD) (mg/dL) | 191.12 (43.20) | 180.68 (32.64) | 192.33 (23.18) | 187.86 (60.56) | 211.78 (43.42) | 197.22 (46.90) | 181.56 (34.30) | 234.67 (25.23) | 171.86 (8.32) |
| HDL cholesterol mean (SD) (mg/dL) | 45.34 (15.18) | 39.70 (13.13) | 51.67 (3.70) | 56.10 (20.69) | 48.20 (15.18) | 45.54 (13.35) | 40.56 (11.46) | 39.97 (10.77) | 47.66 (9.32) |
| LDL cholesterol mean (SD) (mg/dL) | 117.67 (35.94) | 102.48 (22.55) | 138.30 (30.58) | 116.10 (46.91) | 137.46 (35.12) | 124.76 (41.79) | 116.80 (26.99) | 140.11 (38.36) | 92.16 (17.15) |
| Triglycerides mean (SD) (mg/dL) | 161.63 (115.02) | 176.91 (99.71) | 91.67 (19.66) | 90.23 (67.75) | 120.78 (54.97) | 141.94 (81.08) | 188.26 (125.14) | 270.11 (170.20) | 229.00 (154.39) |
| C-reactive protein mean (SD) (mg/L) | 3.42 (3.61) | 2.49 (1.60) | 2.47 (1.69) | 2.36 (2.16) | 4.92 (5.37) | 5.27 (4.88) | 2.99 (2.29) | 1.68 (2.33) | 7.66 (6.70) |

Figure 4:
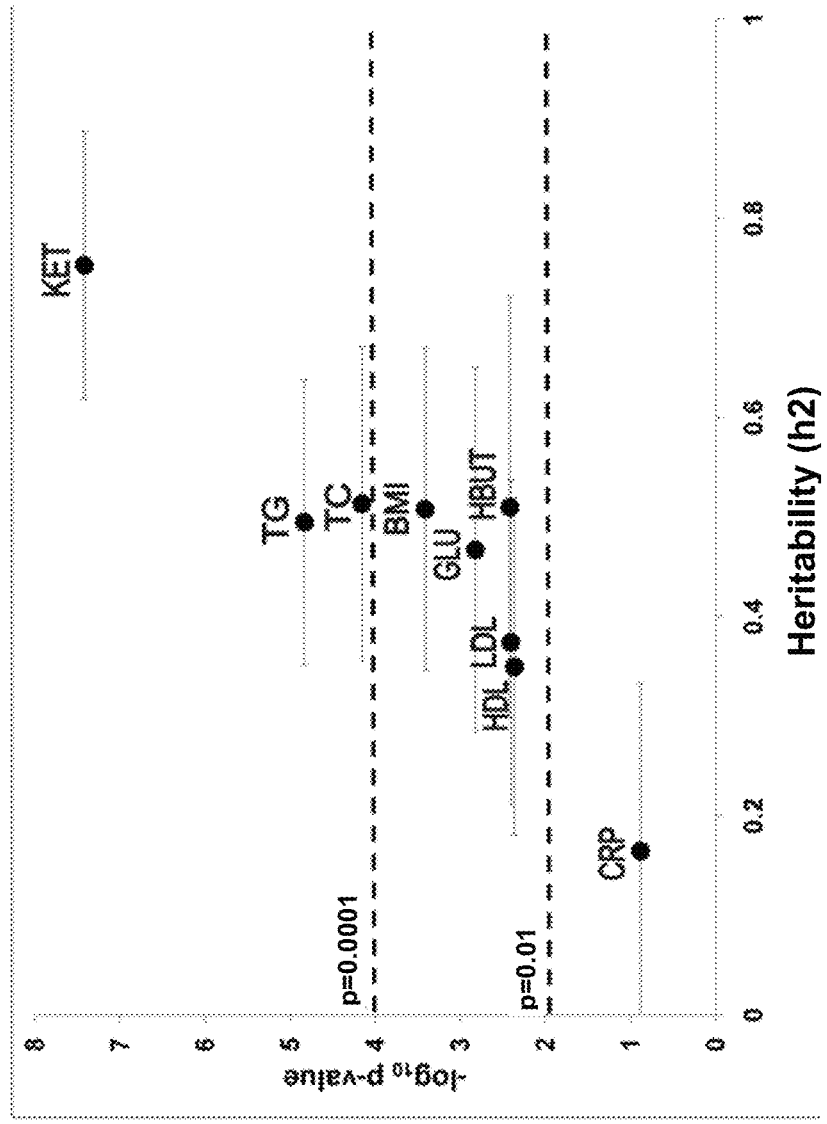
FIG. 4 is a graph showing the heritabilities of conventional metabolites. The Y-axis is the negative log 10 of the p-value for the heritability estimate (X-axis). Error bars around heritability point estimates are in light grey.
Figure 5:
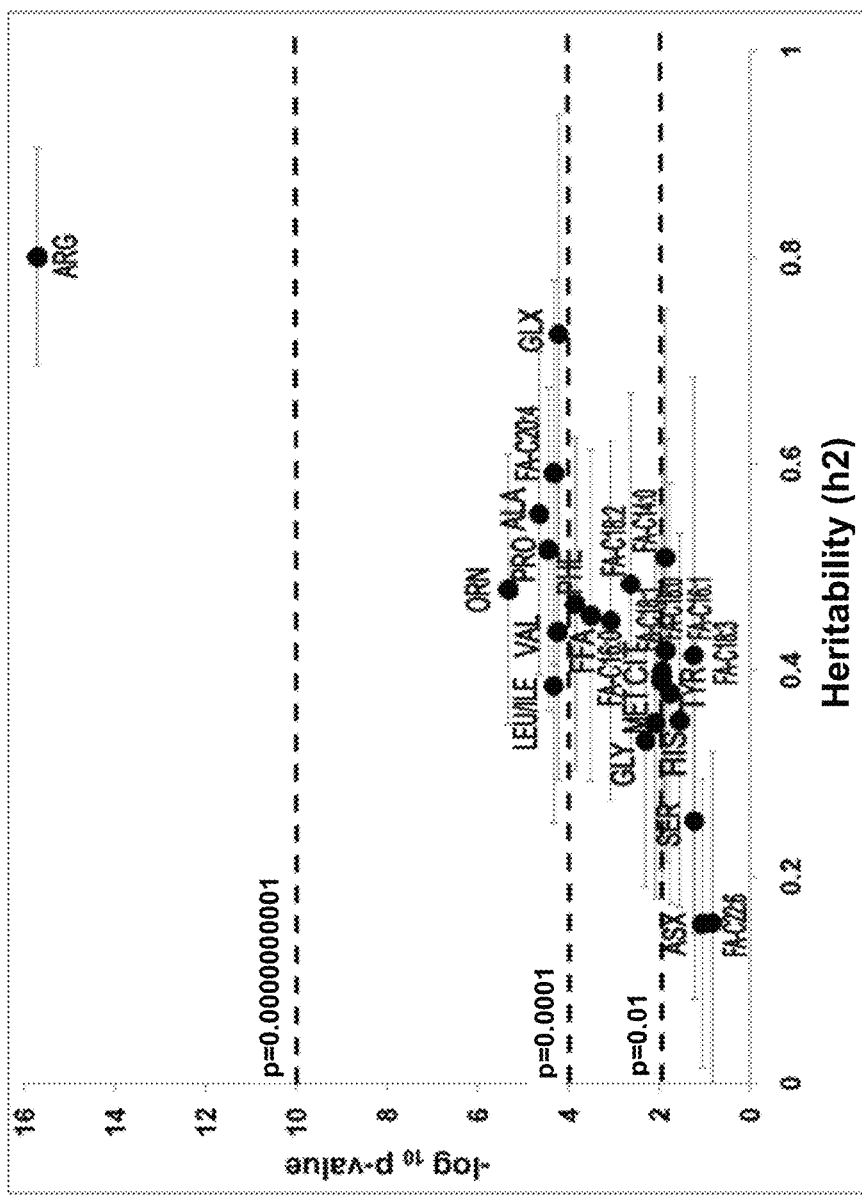
FIG. 5 is a graph showing the heritabilities of amino acids and free fatty acids. Displayed are heritabilities of amino acids and free fatty acids. The Y-axis is the negative log 10 of the p-value for the heritability estimate (X-axis). Error bars around heritability point estimates are in light grey.
Figure 6:
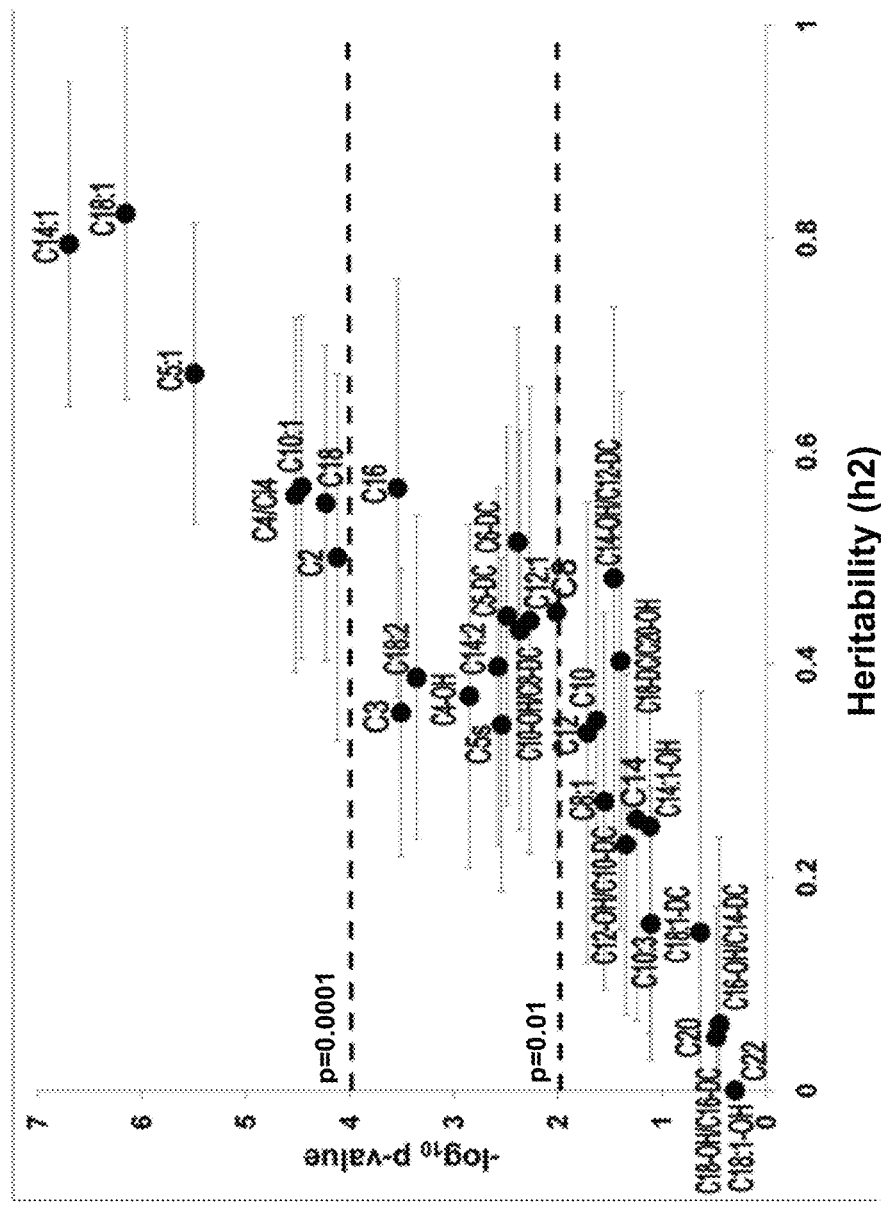
FIG. 6 is a graph showing the heritabilities of acylcarnitines. The Y-axis is the negative log 10 of the p-value for the heritability estimate (X-axis). Error bars around heritability point estimates are in light grey.

HDL: high-density lipoprotein;
LDL: low-density lipoprotein;
BMI: body-mass-index We found high heritabilities for conventional risk factors such as lipids and BMI (FIG. 4). Total ketones ($h^2$ 0.75, $p=3.8\times10^{-8}$) had the highest heritability among the metabolites analyzed by non-mass spectrometry-based methods, with similarly high heritability of the individual ketone β-hydroxybutyrate ($h^2$ 0.51, p=0.004). Among analytes measured by mass spectrometry, several amino acids had high heritability (FIG. 5, Table 14). Arginine (ARG) had the highest score ($h^2$ 0.80, $p=1.9\times10^{-16}$), with strong heritabilities also for glutamine/glutamate (GLX; $h^2$ 0.73, p=0.00006), alanine (ALA; $h^2$ 0.55, p=0.00002), proline (PRO; $h^2$ 0.52, p=0.00004), ornithine (ORN, $h^2$ 0.48, p=0.000005), phenylalanine (PHE; $h^2$ 0.46, p=0.0001), and the branched-chain amino acids leucine/isoleucine (LEU/ILE; $h^2$ 0.39, p=0.00005) and valine (VAL; $h^2$ 0.44, p=0.00006). Of the free fatty acids (FIG. 5), FA-C20:4 (arachidonic acid, a key component in inflammatory pathways) was the most heritable ($h^2$ 0.59, p=0.00005), as well as FA-C18:2 (linoleic acid, precursor to arachidonic acid, $h^2$ 0.48, p=0.002). Many acylcarnitines also had high heritabilities (FIG. 6, Table 14), the highest being the C18 acylcarnitines (C18, C18:1, and C18:2, $h^2$ 0.39-0.82, p=0.0000007-0.004); C14:1 ($h^2$ 0.79, p=0.0000002); C5:1 ($h^2$ 0.67, p=0.000003); the C10s (C10-OH:C8-DC, C10 and C10:1, $h^2$ 0.35-0.57, p=0.00003-0.02); C16 ($h^2$ 0.57, (p=0.0002); C4:Ci4 ($h^2$ 0.56, p=0.00003); short chain dicarboxylacylcarnitines (C5-DC, C6-DC, $h^2$ 0.45-0.51, p=0.003-0.004); and C2 acylcarnitine ($h^2$ 0.50, p=0.00008). Interestingly, estimates for the genetic component of the variability of each metabolite often exceeded the proportion of variance explained by clinical covariates (Table 14).

TABLE 14

Heritabilities, clinical covariates and household effects for individual metabolites. Results for individual metabolites are presented, including: heritability point estimates, standard error for the heritability estimate, clinical covariates found to be significant in the polygenic model, the proportion of variance explained by household effects, the p-value for the household effects, the proportion of variance in the metabolite explained by those clinical covariates, and the p-value for the heritabilities.

| Short Name | Heritability | SE | Covariates* | Proportion Var Household | Household p-value | Proportion Variance Covariates† | Heritability p-value** |
|---|---|---|---|---|---|---|---|
| C2 | 0.50 | 0.17 | Age | 0.06 | 0.3 | 0.18 | 0.00008 |
| C3 | 0.35 | 0.13 | HTN, Sex | 0.08 | 0.06 | 0.18 | 0.0003 |
| C4:Ci4 | 0.56 | 0.17 | CAD, Age, HTN, Dys, Sex | 0.01 | 0.4 | 0.29 | 0.00003 |
| C5:1 | 0.67 | 0.14 | None | 0.02 | 0.4 | N/A | 0.000003 |
| C5 | 0.34 | 0.16 | Sex | 0.00 | N/A | 0.22 | 0.003 |
| C4-OH | 0.37 | 0.16 | Age | 0.04 | 0.2 | 0.05 | 0.001 |
| C8:1 | 0.27 | 0.18 | BMI, Age | 0.00 | N/A | 0.20 | 0.03 |
| C8 | 0.45 | 0.23 | Age | 0.09 | 0.2 | 0.10 | 0.01 |

TABLE 14-continued

Heritabilities, clinical covariates and household effects for individual metabolites. Results for individual metabolites are presented, including: heritability point estimates, standard error for the heritability estimate, clinical covariates found to be significant in the polygenic model, the proportion of variance explained by household effects, the p-value for the household effects, the proportion of variance in the metabolite explained by those clinical covariates, and the p-value for the heritabilities.

| Short Name | Heritability | SE | Covariates* | Proportion Var Household | Household p-value | Proportion Variance Covariates† | Heritability p-value** |
|---|---|---|---|---|---|---|---|
| C5-DC | 0.45 | 0.18 | Age | 0.00 | N/A | 0.05 | 0.003 |
| C6-DC | 0.51 | 0.20 | HTN, Age, Sex | 0.08 | 0.2 | 0.20 | 0.004 |
| C10:3 | 0.16 | 0.13 | Age | 0.00 | N/A | 0.14 | 0.08 |
| C10:1 | 0.57 | 0.16 | Age, Sex | 0.04 | 0.3 | 0.12 | 0.00003 |
| C10 | 0.35 | 0.22 | None | 0.20 | 0.09 | N/A | 0.02 |
| C10OH:C8DC | 0.43 | 0.19 | Age, Sex | 0.00 | N/A | 0.09 | 0.004 |
| C12:1 | 0.44 | 0.22 | DM | 0.00 | 0.5 | 0.003 | 0.005 |
| C12 | 0.34 | 0.22 | Sex | 0.17 | 0.01 | 0.04 | 0.02 |
| C12OH:C10DC | 0.23 | 0.16 | Age, Dys, Sex | 0.00 | N/A | 0.11 | 0.04 |
| C14:2 | 0.40 | 0.17 | None | 0.00 | N/A | N/A | 0.003 |
| C14:1 | 0.79 | 0.15 | DM, Age | 0.00 | N/A | 0.03 | <0.0001 |
| C14 | 0.25 | 0.19 | Dys | 0.18 | 0.05 | 0.04 | 0.06 |
| C14:1-OH | 0.23 | 0.19 | None | 0.01 | 0.4 | N/A | 0.08 |
| C14-OH:12-DC | 0.48 | 0.25 | BMI | 0.02 | 0.4 | 0.003 | 0.03 |
| C16 | 0.57 | 0.20 | BMI, Age | 0.00 | N/A | 0.15 | 0.0003 |
| C16-OH:C14-DC | 0.06 | 0.18 | None | 0.04 | 0.3 | N/A | 0.36 |
| C18:2 | 0.39 | 0.15 | BMI | 0.23 | 0.0007 | 0.11 | 0.0004 |
| C18:1 | 0.82 | 0.17 | BMI, Age | 0.02 | 0.4 | 0.06 | 0.0000007 |
| C18 | 0.55 | 0.15 | BMI, Age, Sex | 0.03 | 0.3 | 0.09 | 0.00006 |
| C18:1-OH | 0.00 | — | None | 0.00 | N/A | N/A | 0.50 |
| C18-OH:C16-DC | 0.00 | — | None | 0.007 | 0.5 | N/A | 0.50 |
| C20 | 0.05 | 0.12 | None | 0.00 | N/A | N/A | 0.33 |
| C18:1-DC | 0.15 | 0.23 | Age | 0.00 | N/A | 0.04 | 0.23 |
| C18-DC:C20-OH | 0.40 | 0.25 | None | 0.00 | N/A | N/A | 0.04 |
| C22 | 0.00 | — | None | 0.08 | 0.2 | N/A | 0.50 |
| GLY | 0.33 | 0.14 | Sex, Dys | 0.09 | 0.09 | 0.15 | 0.005 |
| ALA | 0.55 | 0.16 | BMI | 0.00 | N/A | 0.09 | 0.00002 |
| SER | 0.25 | 0.17 | BMI | 0.19 | 0.02 | 0.13 | 0.06 |
| PRO | 0.52 | 0.16 | Age, Sex | 0.03 | 0.4 | 0.10 | 0.00004 |
| VAL | 0.44 | 0.14 | Age, Sex, BMI | 0.04 | 0.2 | 0.18 | 0.00006 |
| LEU/ILE | 0.39 | 0.13 | Sex | 0.13 | 0.1 | 0.15 | 0.00005 |
| MET | 0.35 | 0.17 | Sex | 0.02 | 0.4 | 0.11 | 0.008 |
| HIS | 0.35 | 0.18 | HTN | 0.02 | 0.4 | 0.04 | 0.03 |
| PHE | 0.46 | 0.16 | Sex, BMI, HTN | 0.00 | N/A | 0.20 | 0.0001 |
| TYR | 0.38 | 0.20 | Sex, BMI | 0.08 | 0.1 | 0.13 | 0.02 |
| ASX | 0.15 | 0.14 | None | 0.32 | 0.01 | N/A | 0.09 |
| GLX | 0.73 | 0.21 | BMI, HTN, Sex | 0.00 | N/A | 0.23 | 0.00006 |
| ORN | 0.48 | 0.13 | Age, BMI, Dys | 0.04 | 0.3 | 0.16 | 0.000005 |
| CIT | 0.39 | 0.18 | CAD, Age | 0.00 | N/A | 0.26 | 0.01 |
| ARG | 0.80 | 0.11 | DM | 0.13 | 0.004 | 0.003 | $1.9 \times 10^{-16}$ |
| FA-C14:0 | 0.51 | 0.24 | DM | 0.00 | N/A | 0.03 | 0.01 |
| FA-C16:1 | 0.42 | 0.20 | DM, Age | 0.00 | N/A | 0.11 | 0.01 |
| FA-C16:0 | 0.45 | 0.17 | None | 0.05 | 0.3 | N/A | 0.0008 |
| FA-C18:3 | 0.41 | 0.27 | DM, CAD, Dys | 0.00 | N/A | 0.08 | 0.06 |
| FA-C18:2 | 0.48 | 0.18 | None | 0.00 | N/A | N/A | 0.002 |
| FA-C18:1 | 0.40 | 0.19 | Age, DM | 0.00 | N/A | 0.13 | 0.01 |
| FA-C18:0 | 0.39 | 0.20 | CAD, Age | 0.08 | 0.3 | 0.06 | 0.01 |
| FA-C20:4 | 0.59 | 0.19 | None | 0.00 | N/A | N/A | 0.00005 |
| FA-C22:6 | 0.16 | 0.16 | None | 0.00 | N/A | N/A | 0.15 |
| FFA | 0.45 | 0.16 | CAD, Age, DM | 0.14 | 0.11 | 0.09 | 0.0003 |
| GLU | 0.47 | 0.18 | DM, Dys, Sex | 0.02 | 0.4 | 0.23 | 0.001 |
| TC | 0.51 | 0.16 | Age, CAD, DM, Dys | 0.09 | 0.08 | 0.14 | 0.00007 |
| HDL | 0.35 | 0.17 | BMI, Sex | 0.00 | N/A | 0.19 | 0.004 |
| LDL | 0.37 | 0.16 | DM, BMI | 0.11 | 0.02 | 0.08 | 0.004 |
| TG | 0.49 | 0.14 | BMI | 0.00 | N/A | 0.05 | 0.00001 |

TABLE 14-continued

Heritabilities, clinical covariates and household effects for individual metabolites. Results for individual metabolites are presented, including: heritability point estimates, standard error for the heritability estimate, clinical covariates found to be significant in the polygenic model, the proportion of variance explained by household effects, the p-value for the household effects, the proportion of variance in the metabolite explained by those clinical covariates, and the p-value for the heritabilities.

| Short Name | Heritability | SE | Covariates* | Proportion Var Household | Household p-value | Proportion Variance Covariates† | Heritability p-value** |
|---|---|---|---|---|---|---|---|
| Ket | 0.75 | 0.13 | None | 0.00 | 0.5 | N/A | $3.8 \times 10^{-8}$ |
| HBut | 0.51 | 0.21 | None | 0.04 | 0.3 | N/A | 0.004 |
| CRP | 0.16 | 0.17 | BMI | 0.09 | 0.2 | 0.20 | 0.13 |
| BMI | 0.51 | 0.16 | Age, HTN | 0.06 | 0.2 | 0.14 | 0.0004 |

*Clinical covariates (age, sex, BMI, hypertension, diabetes, dyslipidemia, CAD status) significant in polygenic model.
†Proportion of variance in metabolite levels accounted for by clinical covariates significant in the model.
**P-value for heritability estimate.
DM: diabetes mellitus;
HTN: hypertension;
BMI: body-mass-index;
CAD: affected with premature CAD;
DYS: dyslipidemia.

Metabolomic Profiles within Families.

Given these strong findings, we sought to understand quantitative differences in metabolites between families. Multivariable linear models were used to test for differences in metabolites between families. Of the amino acids, glutamate, ornithine, arginine, proline, histidine, phenylalanine, alanine and methionine (all p<0.0001), leucine/isoleucine (p<0.0001) and valine (p=0.003) best differentiated families. Of the acylcarnitines, the C18 (C18, C18:1, and C18:2) and the C14 acylcarnitines (C14, C14:1) (all p<0.0001), along with C5:1 (p<0.0001), and C2 (p<0.0001) acylcarnitines best differentiated families. Many free fatty acids differentiated families, the strongest being arachidonic and palmitic acid (both p<0.0001). Of the conventional metabolites, ketones (p<0.0001) and β-hydroxybutyrate (p=0.0001) best differentiated families.

Principal Components Analysis.

Given correlation of metabolites in biological pathways, we performed PCA to understand which clusters of metabolites were correlated and to identify factors that were most heritable. Fifteen factors were identified, demonstrating biologically consistent relationships (Table 15). Factors accounting for the largest amount of variance within the dataset were Factor 1 (short- and medium-chain acylcarnitines); Factor 2 (long-chain free fatty acids); Factor 3 (long-chain acylcarnitines and amino acids [arginine, glutamate/glutamine, and ornithine] possibly reporting on mitochondrial function); Factor 4 (ketones, β-hydroxybutyrate, C2 and C4-OH [β-hydroxybutryl] acylcarnitines; all markers of terminal steps of fatty acid oxidation); and Factor 5 (amino acids, including branched-chain amino acids, and C3 and C5 acylcarnitines [by-products of branched-chain amino acid catabolism]). As expected, given results for individual metabolites, many factors were heritable.

TABLE 15

Principal components analysis in GENECARD. Results of PCA in the dataset are presented, including the key metabolites within each factor (i.e. those with a factor load ≥|0.4|); an overall biochemical description of the key metabolites within each factor; and the eigenvalue, total and cumulative variance, heritability and p-value for the heritability point estimate for each factor.

| Factor | Metabolites within Factor* | Overall Description of Factor | Eigenvalue | Total Var | Cum Var | Heritability (SD) | p-value |
|---|---|---|---|---|---|---|---|
| 1 | C2, C6-DC, C8, C8:1, C10, C10:1, C10:3, C10-OH:C8-DC, C12, C12:1, C14, C14:1, C14:2, C14:1-OH, C14-OH:C12-DC | Short- and medium-chain acylcarnitines | 11.88 | 0.20 | 0.20 | 0.39 (0.16) | 0.0006 |
| 2 | Total FFA, FA-C14:0, FA-C16:0, FA-C16:1, FA-C18:0, FA-C18:1, FA-C18:2, FA-C18:3 | Free fatty acids | 7.55 | 0.13 | 0.32 | 0.35 (0.20) | 0.02 |
| 3 | ARG, GLX, ORN, C16, C18, C18:1, C18:2 | Amino acids, long-chain acylcarnitines (markers of overall | 5.89 | 0.10 | 0.42 | 0.40 (0.18) | 0.002 |

TABLE 15-continued

Principal components analysis in GENECARD. Results of PCA in the dataset are presented, including the key metabolites within each factor (i.e. those with a factor load ≥|0.4|); an overall biochemical description of the key metabolites within each factor; and the eigenvalue, total and cumulative variance, heritability and p-value for the heritability point estimate for each factor.

| Factor | Metabolites within Factor* | Overall Description of Factor | Eigen-value | Total Var | Cum Var | Heritability (SD) | p-value |
|---|---|---|---|---|---|---|---|
| | | mitochondrial function) | | | | | |
| 4 | C2, C4-OH, C14:1, C14:2, C14:1-OH, Ket, Hbut | FFA oxidation byproducts | 3.51 | 0.06 | 0.48 | 0.61 (0.17) | 0.00004 |
| 5 | ALA, LEU/ILE, MET, PRO, TYR, VAL, PHE, C5, C3, C20 | Metabolites involved in amino acid catabolism | 2.98 | 0.05 | 0.53 | 0.27 (0.15) | 0.01 |
| 6 | CIT, C5-DC, C8:1, C10:3 | Various | 2.36 | 0.04 | 0.57 | 0.51 (0.17) | 0.0008 |
| 7 | SER, GLY, CIT, MET | Amino Acids | 2.04 | 0.03 | 0.60 | 0.44 (0.28) | 0.09 |
| 8 | C14-OH:C12-DC, C18:1-OH, C22 | Various | 1.89 | 0.03 | 0.64 | 0.40 (0.18) | 0.003 |
| 9 | C12-OH:C10-DC, C14, C14:1-OH, C20 | Various | 1.86 | 0.03 | 0.67 | 0.51 (0.17) | 0.0003 |
| 10 | C3, C4:Ci4, C22 | Various | 1.67 | 0.03 | 0.69 | 0.46 (0.19) | 0.002 |
| 11 | ASX, HIS | Amino Acids | 1.48 | 0.02 | 0.72 | 0.33 (0.17) | 0.005 |
| 12 | FAC22:6, FAC20:4, C20 | Long chain free fatty acids | 1.37 | 0.02 | 0.74 | 0.36 (0.17) | 0.007 |
| 13 | C16-OH:C14-DC | Various | 1.24 | 0.02 | 0.76 | 0.46 (0.20) | 0.002 |
| 14 | PRO, ALA, C18:1-DC | Various | 1.18 | 0.02 | 0.78 | 0.54 (0.16) | 0.0001 |
| 15 | C18-DC:C20-OH | Various | 1.06 | 0.02 | 0.80 | 0.45 (0.19) | 0.006 |

*Factor load ≥|0.4|;
FFA: free fatty acids;
Tot Var: total variance;
Cum Var: cumulative variance A comprehensive set of analytical tools was applied to gain a better understanding of the biochemical and physiologic underpinnings of cardiovascular disease, and how metabolomic profiles may relate to the known genetic component of CAD risk. Targeted, quantitative metabolic profiling was performed in multiplex families burdened with premature CAD, the majority representing offspring of the affected generation that had not yet developed CAD, but in whom we hypothesized similar metabolic profiles as their affected family members, if such profiles were heritable. High heritabilities were found for many metabolites, many with higher heritabilities than for conventional risk factors. These high heritabilities suggest a strong correlation between genotype and phenotype, implying a strong genetic component to clustering of these metabolic signatures in families burdened with CAD.

In addition, several individual metabolites distinguished families, the most prominent being, among the amino acids, arginine, ornithine, and glutamate/glutamine; and among the lipid-derived metabolites, the long-chain acylcarnitines C18:0, C18:1, and C18:2. These findings suggest fundamental differences in mitochondrial function in these families, consistent with prior studies showing relationships between impaired mitochondrial function and insulin resistance.

Given our studies were hypothesis-generating, we did not adjust for multiple comparisons. However, with a Bonferroni correction at the level of the factors, nine factors remain significant (p<0.003). We did not account for dietary pattern (known influence on metabolites), renal function, or medications (unknown influence). To help minimize these "non-genetic" effects, we incorporated a household effect and included married-in individuals, partially controlling for shared nutritional and other environmental effects. The measures of household effects suggest minimal influence on heritability estimates with high heritabilities despite adjustment. Therefore, we believe our results reflect both underlying genetic and environmental effects, similar to traditional cholesterol parameters. Accordingly, we found a significant household effect for LDL cholesterol (proportion of variance due to household 0.11, p=0.02), but with a significant heritability despite adjustment for this environmental effect ($h^2$ 0.37, p=0.004).

Similarly, results could reflect differences in essential versus non-essential metabolites. However, we found similar heritabilities for the essential ($h^2$=0.40, p=0.0004) and non-essential ($h^2$=0.63, p=0.00002) amino acids when analyzed as groups, and for the essential ($h^2$=0.50, p=0.003) compared with the non-essential ($h^2$=0.33, p=0.03) fatty acids. Although underpowered for such analyses, we also examined the relationship of age with heritabilities related to these groups. Age was a significant covariate on heritability estimates for both essential (valine) and nonessential (proline, ornithine, citrulline) amino acids (Table 14). For the free fatty acids, age was a covariate only for nonessential fatty acids (palmitoleic, oleic and stearic acid). We also examined correlations of metabolites with age and found that both essential (tyrosine, linoleic acid) and non-essential (glutamine, ornithine, citrulline, oleic acid) metabolites were significantly correlated with age (data not shown). Therefore, there does not seem to be a consistent variation of metabolites with age, nor with heritability estimates, based on essential/non-essential groups. This may indicate that fundamental and genetically controlled metabolic processes (e.g. mitochondrial or microsomal catabolic pathways) are influencing the levels of both essential and non-essential metabolites that utilize these common elements of the metabolic machinery.

Other factors that could impact heritability estimates include variability in sample collection or processing. We used a standardized protocol to limit this type of variability, intra-individual variation was low in a set of repeated assays, and family members were collected at different locations and times.

A major strength of the study is the use of a very accurate, targeted, quantitative approach to metabolomic profiling, allowing us to dissect biological mechanisms underlying CAD pathophysiology. In addition to furthering the understanding of CAD pathophysiology, these results may have significant implications for risk prediction.

Each of the references cited herein is hereby incorporated by reference in its entirety.

We claim:

1. A method for treating a subject having an increased risk of cardiovascular disease, the method comprising:
    (a) determining using mass spectrometry in a sample from the subject the level of each metabolite in a group of metabolites consisting of C5-DC, C6-DC, C8:1-DC, and C8:1-OH/C6:1-DC, wherein C8:1-OH/C6:1-DC is C8:1-OH, or C6:1-DC, or a combination of C8:1-OH and C6:1-DC, wherein the level of each metabolite multiplied by a loading factor specific for each metabolite determines a weighted level of each metabolite, and wherein the weighted level of each metabolite added together yields a factor score in the subject that is different from a factor score in a non-cardiovascular disease standard;
    (b) diagnosing the subject as having an increased risk of cardiovascular disease based on the factor score in the subject determined in step (a); and
    (c) administering a pharmaceutical therapy to the subject.

2. The method of claim 1, wherein the cardiovascular disease is a cardiovascular event and the factor score in the subject being different from the standard is indicative of the risk of a cardiovascular event in the subject.

3. The method of claim 1, wherein the cardiovascular disease is coronary artery disease and the factor score in the subject being different from the standard is indicative of the presence of coronary artery disease in the subject.

4. The method of claim 1, wherein the cardiovascular disease is coronary artery disease and the factor score in the subject being different from the standard is indicative of the risk of developing coronary artery disease in the subject.

5. The method of claim 1, wherein the sample is blood.

6. The method of claim 1, wherein 08:1-OH/C6:1-DC is 08:1-OH.

7. The method of claim 1, wherein 08:1-OH/C6:1-DC is C6:1-DC.

8. The method of claim 1, wherein 08:1-OH/C6:1-DC is a combination of C8:1-OH and C6:1-DC.

9. A method for treating a subject having an increased risk of cardiovascular disease, the method consisting of:
    (a) detecting using mass spectrometry in a sample from the subject the level of each metabolite in a group of metabolites consisting of C5-DC, C6-DC, C8:1-DC, and C8:1-OH/C6:1-DC, wherein C8:1-OH/C6:1-DC is C8:1-OH, or C6:1-DC, or a combination of C8:1-OH and C6:1-DC, the detected level of each metabolite in the subject being different from the level in a non-cardiovascular disease standard;
    (b) diagnosing the subject as having an increased risk of cardiovascular disease based on the detected level of each metabolite in the subject in step (a); and
    (c) administering a pharmaceutical therapy to the subject.

10. The method of claim 9, wherein the cardiovascular disease is a cardiovascular event and the different level of each metabolite is indicative of the risk of a cardiovascular event in the subject.

11. The method of claim 9, wherein the cardiovascular disease is coronary artery disease and the different level of each metabolite is indicative of the presence of coronary artery disease in the subject.

12. The method of claim 9, wherein the cardiovascular disease is coronary artery disease and the different level of each metabolite is indicative of the risk of developing coronary artery disease in the subject.

13. The method of claim 9, wherein the sample is blood.

14. The method of claim 9, wherein 08:1-OH/C6:1-DC is 08:1-OH.

15. The method of claim 9, wherein 08:1-OH/C6:1-DC is C6:1-DC.

16. The method of claim 9, wherein 08:1-OH/C6:1-DC is a combination of C8:1-OH and C6:1-DC.

* * * * *